US012715851B2

(12) United States Patent
Kaschula et al.

(10) Patent No.: US 12,715,851 B2
(45) Date of Patent: Aug. 25, 2026

(54) 4'-SUBSTITUTED ANALOGUES OF FISETIN AND THEIR USE IN THE TREATMENT OF CANCER

(71) Applicants: Stellenbosch University, Stellenbosch (ZA); Jawaharlal Nehru University, New Delhi (IN)

(72) Inventors: Catherine Hart Kaschula, Stellenbosch (CA); Rana Pratap Singh, New Delhi (IN); Arpit Dheeraj, New Delhi (IN); Akash Sabarwal, New Delhi (IN)

(73) Assignees: Stellenbosch University, Stellenbosch (ZA); Jawaharlal Nehru University, New Delhi (IN)

( * ) Notice: Subject to any disclaimer, the term of this patent is extended or adjusted under 35 U.S.C. 154(b) by 516 days.

(21) Appl. No.: 18/039,397

(22) PCT Filed: Nov. 30, 2021

(86) PCT No.: PCT/IB2021/061110
§ 371 (c)(1),
(2) Date: May 30, 2023

(87) PCT Pub. No.: WO2022/113047
PCT Pub. Date: Jun. 2, 2022

(65) Prior Publication Data

US 2024/0002357 A1 Jan. 4, 2024

(30) Foreign Application Priority Data

Nov. 30, 2020 (IN) ............................ 202021052123

(51) Int. Cl.
*C07D 311/30* (2006.01)
*A61P 35/00* (2006.01)

(52) U.S. Cl.
CPC ............ *C07D 311/30* (2013.01); *A61P 35/00* (2018.01)

(58) Field of Classification Search
CPC .................................................. C07D 311/30
See application file for complete search history.

(56) References Cited

FOREIGN PATENT DOCUMENTS

| | | | |
|---|---|---|---|
| CN | 1837202 | A | 9/2006 |
| JP | 2004067551 | A | 3/2004 |
| WO | WO01/12496 | A1 * | 3/2000 |
| WO | 0012496 | A1 | 9/2000 |
| WO | 2008076767 | A1 | 6/2008 |

(Continued)

OTHER PUBLICATIONS

Zhang et al. (The Scientific World Journal, 2013, 649485, 6 pages, 2013) (Year: 2013).*

(Continued)

*Primary Examiner* — Brandon J Fetterolf
(74) *Attorney, Agent, or Firm* — Meunier Carlin & Curfman LLC

(57) ABSTRACT

This invention relates to compounds that are 4'-substituted analogues of the flavonol Fisetin. In particular, the invention relates to such compounds wherein the 4' position on the B-ring is substituted with a ring deactivating group which has a para-Hammett constant greater than zero, and the use of these compounds in the treatment of cancer, including epithelial cancers.

15 Claims, 11 Drawing Sheets

(1)

1

(2)

2, Chalcone (3, 4)

3, Flavonol

| No. | $R_5$ | $R_6$ | $R_7$ | X |
|---|---|---|---|---|
| 1a | H | H | OMOM | - |
| 1b | H | OMOM | H | - |
| 1c | OMOM | H | H | - |
| 2a | H | H | H | Br |
| 2b | H | H | OMOM | Br |
| 2c | H | OMOM | H | Br |
| 2d | OMOM | H | H | Br |
| 2e | H | H | OMOM | Cl |
| 2f | H | H | OMOM | F |
| 2g | H | H | OMOM | I |
| 2h | H | H | OMOM | $CH_3$ |
| 2i | H | H | OMOM | OMOM |
| 2j | H | H | OMOM | OMe |
| 2k | H | H | OMOM | H |
| 3a | H | H | H | Br |
| 3b | H | H | OMOM | Br |
| 3c | H | H | OH | Br |
| 3d | H | OMOM | H | Br |
| 3e | H | OH | H | Br |
| 3f | OH | H | H | Br |
| 3g | H | H | OH | Cl |
| 3h | H | H | OH | F |
| 3i | H | H | OH | I |
| 3j | H | H | OH | $CH_3$ |
| 3k | H | H | OH | H |
| 3l | H | H | OH | OH |
| 3m | H | H | OH | OMe |
| 3n | H | H | OH | $CF_3$ |
| 3o | H | H | OH | SMe |
| 3p | H | H | OH | $SO_2CH_3$ |

(56) References Cited

FOREIGN PATENT DOCUMENTS

WO 2010060891 A1 6/2010

OTHER PUBLICATIONS

Lee et al. (Bioorg. Med. Chem. Lett. 2010; 20: 5709-5712) (Year: 2010).*

International Search Report and Written Opinion received in PCT/IB2021/061110 mailed Feb. 3, 2022.

Forbes et al. "Synthesis and anticancer activity of new flavonoid analogs and inconsistencies in assays related to proliferation and viability measurements", International Journal of Oncology, vol. 45, No. 2, Aug. 1, 2014 (Aug. 1, 2014), pp. 831-842, XP055882854, GR ISSN: 1019-6439, DOI: 10.3892/ijo.2014.2452 figure 2; tables I-IV; compounds Sb, (X=I), Sd (X=COPh).

Kim et al. "Synthesis and Biological Evaluation of 4'-Substituted Kaempfer-3-ols", The Journal of Organic Chemistry, vol. 85, No. 6, Mar. 20, 2020 (Mar. 20, 2020), pp. 4279-4288, XP055882450, ISSN: 0022-3263, DOI: 10.1021/acs.joc.9b03461 Retrieved from the Internet: URL:https://pubs.acs.org/doi/pdf/10.1021/acs.joc.9b03461> figure 1; table 1; compounds 3b, 3c.

Znati et al."Synthesis, molecular properties, anti-inflammatory and anticancer activities of novel 3-hydroxyflavone derivatives", Bioorganic Chemistry, vol. 89, Aug. 1, 2019 (Aug. 1, 2019), p. 103009, XP055882861, us ISSN: 0045-2068, DOI: 10.1016/j.bioorg.2019.103009 p. 2-p. 3; table 1; compound 43 (see scheme 1).

Edwards et al. "Antineoplastic Activity and Cytotoxicity of Flavones, Isoflavones, and Flavanones", Journal of Natural Products, American Chemical Society, US, vol. 42, No. 1, Jan. 1, 1979 (Jan. 1, 1979), pp. 85-91, XP009035912, ISSN: 0163-3864, DOI: 10.1021/NP50001A002 table 1; compound 46668 (p. 87).

Kamble et al. "Synthesis, In Vitro Antioxidant and Antimicrobial Evaluation of 3-Hydroxy Chromone Derivatives", International Journal of Chemtech Research (Print), Jan. 1, 2018 (Jan. 1, 2018), XP055882822, India ISSN: 0974-4290, DOI: 10.20902/IJCTR.2018.110209 Retrieved from the Internet: URL:https://sphinxsai.com/2018/ch_volll_no2/1/(63-76)V11N02CT.pdf>table 1 (pp. 69ff.); compounds D15, D17, DI8, D21.

Avani et al. "A facile synthetic approach for the syntheses of 7-hydroxyflavonol derivatives", Der Pharma Chemica, Jan. 1, 2015 (Jan. 1, 2015), pp. 142-146, XP055883029, table 1; compound 8.

Fillaut et al. "Flavonol based ruthenium acetylides as fluorescent chemosensors for lead ions", Journal of Organometallic Chemistry, Elsevier, Amsterdam, NL, vol. 693, No. 2, Nov. 4, 2007 (Nov. 4, 2007), pp. 228-234, XP022399440, ISSN: 0022-328X, DOI: 10.1016/J.JORGANCHEM.2007.10.046 compound 4b (Scheme 1).

Xiong et al. "Synthesis of Flavonols via Pyrrolidine Catalysis: Origins of the Selectivity for Flavonol versus Aurone", The Journal of Organic Chemistry, vol. 85, No. 20, Oct. 16, 2020 (Oct. 16, 2020), pp. 13160-13176, XP055882828, ISSN: 0022-3263, DOI: 10.1021/acs.joc.0c01869 table 2; compounds C6, C7, CS (p. 13163).

Golub A.G., et al., "Structure-Based Discovery of Novel Flavonol Inhibitors of Human Protein Kinase CK2," Molecular and Cellular Biochemistry, 2011, vol. 356, pp. 107-115.

Kalkbrenner F., et al., "In Vitro Inhibition and Stimulation of Purified Prostaglandin Endoperoxide Synthase by Flavonoids: Structure-Activity Relationship," Pharmacology, 1992, vol. 44, pp. 1-12.

Lee H.S., et al., "7-O-Arylmethylgalangin as a Novel Scaffold for Anti-HCV Agents," Bioorganic & Medicinal Chemistry Letters, 2010, vol. 20, pp. 5709-5712.

Mei Q., et al., "Selective Methylation of Kaempferol via Benzylation and Deacetylation of Kaempferol Acetates," Beilstein Journal of Organic Chemistry, 2015, vol. 11, pp. 288-293.

Sato K., et al., "Carboxy Flavonoids. IV. Synthesis and Reactions of 4'-Carboxy Flavanones," Akita Daigaku Kyoikugakubu Kenkyu Kiyo, Shizen Kagaku, 1988, No. 39, pp. 117-124.

Xiong W., et al., "Synthesis of Flavonols via Pyrrolidine Catalysis: Origins of the Selectivity forAurone," Supporting Information, The Journal of Organic Chemistry, 2020, vol. 85, No. 20, pp. S1-S89 (89 pages).

* cited by examiner

1

2, Chalcone

3, Flavonol

| No. | $R_5$ | $R_6$ | $R_7$ | X |
|---|---|---|---|---|
| 1a | H | H | OMOM | - |
| 1b | H | OMOM | H | - |
| 1c | OMOM | H | H | - |
| 2a | H | H | H | Br |
| 2b | H | H | OMOM | Br |
| 2c | H | OMOM | H | Br |
| 2d | OMOM | H | H | Br |
| 2e | H | H | OMOM | Cl |
| 2f | H | H | OMOM | F |
| 2g | H | H | OMOM | I |
| 2h | H | H | OMOM | $CH_3$ |
| 2i | H | H | OMOM | OMOM |
| 2j | H | H | OMOM | OMe |
| 2k | H | H | OMOM | H |
| 3a | H | H | H | Br |
| 3b | H | H | OMOM | Br |
| 3c | H | H | OH | Br |
| 3d | H | OMOM | H | Br |
| 3e | H | OH | H | Br |
| 3f | OH | H | H | Br |
| 3g | H | H | OH | C1 |
| 3h | H | H | OH | F |
| 3i | H | H | OH | I |
| 3j | H | H | OH | $CH_3$ |
| 3k | H | H | OH | H |
| 3l | H | H | OH | OH |
| 3m | H | H | OH | OMe |
| 3n | H | H | OH | $CF_3$ |
| 3o | H | H | OH | SMe |
| 3p | H | H | OH | $SO_2CH_3$ |

| No. | 4'-X | $IC_{50}$±SD / μM | | $LogIC_{50}$ | $\sigma_p$ |
|---|---|---|---|---|---|
| 3c | Br | 18.0±8.4 | (n=8) | 1.254 | 0.23 |
| 3g | Cl | 17.9±7.8 | (n=9) | 1.252 | 0.23 |
| 3i | I | 26.4±10.2 | (n=5) | 1.421 | 0.18 |
| 3h | F | 37.6±13.5 | (n=7) | 1.575 | 0.06 |
| 3j | $CH_3$ | 104.3±49.2 | (n=4) | 2.018 | -0.17 |
| 3k | H | 75.4±22.6 | (n=5) | 1.877 | 0.00 |
| 3l | OH | 147.6±74.8 | (n=6) | 2.169 | -0.37 |
| 3m | OMe | 21.7±10.3 | (n=3) | 1.337 | -0.27 |
| 3n | $CF_3$ | 7.25±2.55 | (n=5) | 0.860 | 0.54 |
| 3o | SMe | 50.9±14.6 | (n=2) | 1.707 | 0.00 |
| 3p | $SO_2CH_3$ | 2.41±1.09 | (n=2) | 0.386 | 0.72 |

D

| Parameters/ Treatments | Control | B(a)P | FS+B(a)P | FSA(3c)+ B(a)P | B(a)P+FS | B(a)P+ FSA(3c) |
|---|---|---|---|---|---|---|
| Number of Animals | 5 | 5 | 5 | 5 | 5 | 5 |
| Tumor incidence (Gross observation at External Surface of Lung) | 0 | 5/5 | 2/5 | 1/5 | 3/5 | 2/5 |
| Tumor incidence (Through Histopathology) | 1/5 | 5/5 | 3/5 | 4/5 | 3/5 | 3/5 |

4'-SUBSTITUTED ANALOGUES OF FISETIN AND THEIR USE IN THE TREATMENT OF CANCER

INTRODUCTION

This invention relates to novel compounds that are 4'-substituted analogues of the flavonol Fisetin. The invention further provides for pharmaceutical compositions comprising these compounds, and the use of these compounds and compositions in the treatment of cancer, in particular but not exclusively, in the treatment of epithelial cancers.

BACKGROUND

This invention relates to analogues of Fisetin substituted with ring-deactivating groups at the 4'-position of the B-ring. In particular, but not exclusively, the invention relates to analogues of Fisetin substituted with ring-deactivating groups at the 4'-position which are useful as chemotherapeutic agents in the treatment of epithelial cancers, in particular lung cancer.

Flavonols have been shown to induce cytotoxicity in a number of different cancer cell lines including leukaemia, breast, prostate, lung, colon and skin. These compounds may exert their biological activity via a number of mechanisms that could involve antioxidant or redox modulation, protein binding and enzyme inhibition, as well as metal complexation.

Due to the broad spectrum of possible targets, the task of correlating structural features of flavonols to cancer cell cytotoxicity is complex depending on the specific flavonol, its target, and the cancer type under investigation. Fisetin is a naturally occurring flavonol found in a wide variety of medicinal and edible plants, and has been shown to inhibit cancer growth through alteration of cell cycle, inducing apoptosis, angiogenesis, invasion, and metastasis without causing any toxicity to normal cells.

Certain generalisations have been made about the flavonoid template, with flavones and flavonols having been reported to be more active than chalcones and flavanones. This highlights the importance of the 2,3-double bond in cancer cell cytotoxicity. For example, navingenin is reported to be inactive compared to its 2,3-unsaturated family member apigenin against a range of cancer cell lines. Furthermore, the presence of the 3-hydroxy group appears not to be critical for cancer cell cytotoxicity. For example, methylation of this position in the synthetic flavonol, TMFol, results in retention of its low micromolar activity against 22rv1 prostate carcinoma cells.

In a large library of synthetic flavonoids (79 compounds), it has been concluded that 3-methoxy substitution is desirable for enhanced cytotoxicity and tubulin binding. In another study, the longer propyloxy group has been found to be more potent than the methoxy derivative. The methylation of flavonoid hydroxyl groups is reported to favourably improve the metabolic stability of these compounds. Natural flavonols are typically glycosylated at the 3 or 4'-positions. The most acidic position in Fisetin (or quercetin) is the 7-hydroxyl group ($pK_a$~7.3), followed by the 4'-hydroxyl group ($pK_a$~9.4).

From the literature, there is no clear indication of the substitution patterns that are favourable for improved cytotoxicity. This is partly because conclusions are drawn based on small subsets of compounds synthesised, and because there are an infinite number of possible permutations. Most studies have looked at the effect of O-alkylation on the cytotoxicity of the flavonol, which appears to be favourable over hydroxylation in most studies. Importantly, methoxylation at positions 3' and 4' is reported, in more than one instance, to be favourable.

The cytotoxic effects of 4'-substituted analogues of Fisetin in various cancers including lung cancer cells are not known, and a need exists to synthesise such analogues and establish their effectiveness against lung cancer.

It is an object of this invention to synthesise analogues of Fisetin, substituted at the 4'-position, that are designed to have favourable cytotoxicity against epithelial cancer cells, in particular lung cancer cells, useful as a chemotherapeutic agent in the treatment of epithelial cancers, in particular lung cancer.

SUMMARY OF THE INVENTION

In accordance with a first aspect of the invention there is provided a compound of Formula I:

I

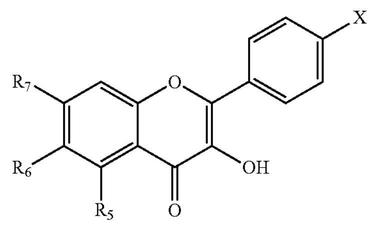

or a pharmaceutically acceptable salt or solvate thereof, wherein:

X is a ring deactivating group selected from —Br, —Cl, —F, —I, $—SO_2F$, $—SF_5$, —NO, $—NO_2$, $—SO_2NH_2$, $—N{=}CCl_2$, $—CF_3$, $—OCF_3$, $—SCF_3$, —CN, —NCS, —SCN, $—SCH_3$, $—SO_2CF_3$, —NHCN, —CHO, $—CO_2H$, —NHCHO, $—CONH_2$, —CH═NOH, $—NHCSNH_2$, $—SOCH_3$, $—OSO_2CH_3$, $—SO_2CH_3$, $—NHSO_2CH_3$, $—CF_3CF_3$, —C═CH, —NHCOCF, $CH_2CN$, $—CH{=}CHNO_2$, $—COCH_3$, $—SCOCH_3$, —OCOCH, $—PMe_2$, $—CO_2C_2H_5$, $—CO_2CH_3$, $—CONHCH_3$, $—SO_2C_2H_5$, $—COC_3H_7$, $—CO_2C_3H_7$, $—N{=}NC_6H_5$, $—SO_2C_6H_5$, $—OSO_2C_6H_5$ and $—COC_6H_5$, and $—CN{=}NC_6H_5$;

$R_7$, $R_6$, and $R_5$ are independently selected from H, OH, $—O(CH_2)OR_4$, and $—OR_4$, provided that at least one of $R_7$, $R_6$, and $R_5$ is OH, $—O(CH_2)OR_4$, or $—OR_4$; and $R_4$ is selected from the group consisting of $C_1$-$C_6$ alkyl, $C_1$-$C_6$ heteroalkyl, $C_1$-$C_6$ aryl, or $C_1$-$C_6$ heteroaryl.

Preferably, X is selected from Br, Cl, F, I, $CF_3$, and $—SO_2CH_3$.

Most preferably, X is Br, Cl, $CF_3$, or $—SO_2CH_3$.

In one embodiment, $R_6$, and $R_5$ are H and $R_7$ is OH.

In another embodiment, $R_7$, and $R_5$ are H and $R_6$ is OH.

In yet another embodiment, $R_7$, and $R_6$ are H and $R_5$ is OH.

In yet another embodiment, $R_6$, and $R_5$ are H and $R_7$ is $—OCH_3$, $—OCH_2CH_3$, or $—O(CH_2)OCH_3$.

In yet another embodiment, $R_7$, and $R_5$ are H and $R_6$ is $—OCH_3$, $—OCH_2CH_3$, $—O(CH_2)OCH_3$.

In accordance with a second aspect of the invention there is provided a pharmaceutical composition comprising a compound of Formula I or a pharmaceutically acceptable salt or solvate thereof, and one or more pharmaceutically acceptable vehicles.

In accordance with a third aspect of the invention there is provided a compound of Formula I:

I

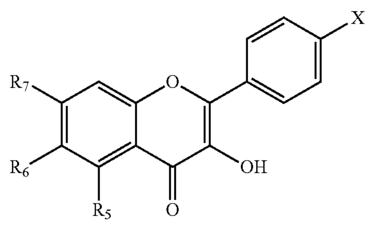

or a pharmaceutically acceptable salt or solvate thereof, wherein:

X is a ring deactivating group having a para-Hammett constant greater than zero, or wherein X is $-OCH_3$, and $R_7$, $R_6$, and $R_5$ are independently selected from H, OH, $-O(CH_2)OR_4$, and $-OR_4$, provided that at least one of $R_7$, $R_6$, and $R_5$ is OH, $-O(CH_2)OR_4$, or $-OR_4$; and $R_4$ is selected from the group consisting of $C_1$-$C_6$ alkyl, $C_1$-$C_6$ heteroalkyl, $C_1$-$C_6$ aryl, or $C_1$-$C_6$ heteroaryl, for use in a method of treating cancer in a subject, the method comprising administering a therapeutically effective amount of the compound, therapeutically acceptable salt or solvate thereof to the subject.

In one embodiment of the invention, X is a ring deactivating group selected from —Br, —Cl, —F, —I, $-SO_2F$, $-SF_5$, —NO, $-NO_2$, $-SO_2NH_2$, $-N{=}CCl_2$, $-CF_3$, $-OCF_3$, $-SCF_3$, —CN, —NCS, —SCN, $-SCH_3$, $-SO_2CF_3$, —NHCN, —CHO, $-CO_2H$, —NHCHO, $-CONH_2$, —CH=NOH, $-NHCSNH_2$, $-SOCH_3$, $-OSO_2CH_3$, $-SO_2CH_3$, $-NHSO_2CH_3$, $-CF_3CF_3$, —C=CH, —NHCOCF, $CH_2CN$, $-CH{=}CHNO_2$, $-COCH_3$, $-SCOCH_3$, —OCOCH, $-PMe_2$, $-CO_2C_2H_5$, $-CO_2CH_3$, $-CONHCH_3$, $-SO_2C_2H_5$, $-COC_3H_7$, $-CO_2C_3H_7$, $-N{=}NC_6H_5$, $-SO_2C_6H_5$, $-OSO_2C_6H_5$ and $-COC_6H_5$, and $-CN{=}NC_6H_5$.

Preferably, X is selected from Br, Cl, F, I, $CF_3$, and $-SO_2CH_3$.

Most preferably, X is Br, $CF_3$, or $-SO_2CH_3$.

In one embodiment, $R_7$, $R_6$, and $R_5$ are H.

Preferably, the cancer is a cancer derived from epithelial cells including lung cancer, breast cancer, prostate cancer, cancer of the pancreas, and colon cancer.

Most preferably, the cancer is lung cancer.

In accordance with a fourth aspect of the invention there is provided for the use of compound, pharmaceutically acceptable salt of solvate thereof of the invention in the preparation of a medicament for treating cancer in a subject, the method comprising administering the medicament comprising a therapeutically effective amount of the compound, therapeutically acceptable salt or solvate thereof to the subject.

BRIEF DESCRIPTION OF THE FIGURES

Non-limiting embodiments of the invention will now be described by way of example only, and with reference to the following figure.

DETAILED DESCRIPTION OF THE INVENTION

Figure 1:
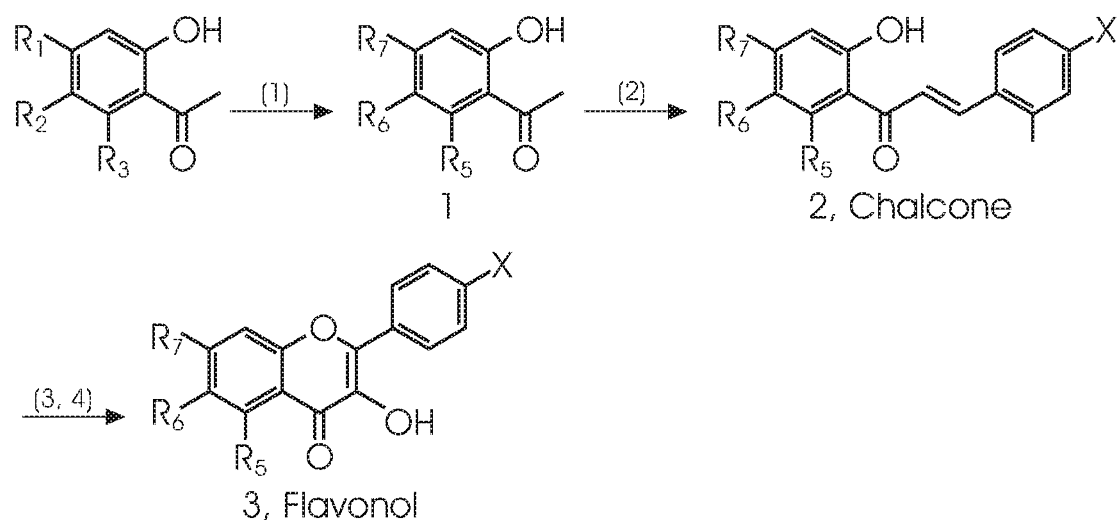
FIG. 1 shows the synthetic route to analogues of Fisetin and a table of the relevant compounds indicating the various substituents $R_5$, $R_6$, $R_7$, and X for each.

The present invention will now be described more fully hereinafter, wherein some, but not all embodiments of the invention are described.

The invention as described should not to be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

When describing the invention, which includes compounds, pharmaceutical compositions containing such compounds and methods of using such compounds and compositions, the following terms, if present, have the following meanings, unless otherwise indicated. It should also be understood that when described herein any of the moieties defined forth below may be substituted with a variety of substituents, and that the respective definitions are intended to include such substituted moieties within their scope as set out below. In this regard, unless otherwise stated, the term "substituted" is to be defined as set out below. It should be further understood that, unless the context clearly indicates otherwise, the terms "groups" and "radicals" can be considered interchangeable when used herein.

As used herein, the term "flavone" is a compound of the following general structure:

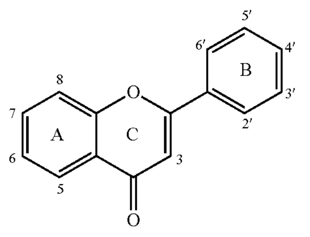

with "A-ring", "B-ring" and "C-ring" corresponding to the rings shown in the above flavonoid structure, and the positions on the flavonoid indicated by the numbers in the above structure. The corresponding positions and ring structure of "flavonol" is shown in the following general structure:

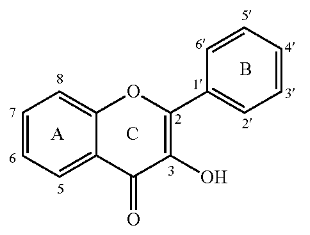

"Pharmaceutically acceptable" means approved or approvable by a regulatory agency such as the United States Food and Drug Administration agency, or any similar agency in countries other than the United States, or that is listed in the a generally recognized pharmacopoeia for use in animals, and more particularly in humans, such as the U.S. Pharmacopoeia.

"Pharmaceutically acceptable salt" refers to a salt of a compound of the invention that is pharmaceutically acceptable and that possesses the desired pharmacological activity of the parent compound. In particular, such salts are non-toxic and may be inorganic or organic acid addition salts and base addition salts. Specifically, such salts may include: (1) acid addition salts, formed with inorganic acids including: hydrochloric acid, hydrobromic acid, sulfuric acid, nitric acid, and phosphoric acid; or formed with organic acids including: acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid; or (2) salts formed when an acidic proton present in the parent compound either is replaced by a metal ion, e.g. an alkali metal ion, an alkaline earth ion, or an aluminum ion; or coordinates with an organic base including ethanolamine, diethanolamine, triethanolamine, and N-methylglucamine. Salts further include, by way of example only, sodium, potassium, calcium, magnesium, ammonium, and tetraalkylammonium; and when the compound contains a basic functionality, salts of non-toxic organic or inorganic acids, including hydrochloride, hydrobromide, tartrate, mesylate, acetate, maleate, and oxalate. The term 'pharmaceutically acceptable cation' refers to an acceptable cationic counter-ion of an acidic functional group. Such cations are exemplified by sodium, potassium, calcium, magnesium, ammonium, and tetraalkylammonium cations.

"Pharmaceutically acceptable vehicle" refers to a diluent, adjuvant, excipient or carrier with which a compound of the invention is administered.

"Solvate" refers to forms of the compound that are associated with a solvent, usually by a solvolysis reaction. This physical association includes hydrogen bonding. Conventional solvents include, by way of example, water, ethanol, and acetic acid. The compounds of the invention may be prepared, for example, in crystalline form and may then be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

"Subject" includes humans. The terms "human", "patient" and "subject" are used interchangeably herein.

"Effective amount" means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

"Treating" or "treatment" of any disease or disorder includes ameliorating the disease or disorder, i.e. arresting the disease or reducing the manifestation, extent or severity of at least one of the clinical symptoms thereof. In another embodiment "treating" or "treatment" refers to ameliorating at least one physical parameter, which may not be discernible by the subject. In yet another embodiment, "treating' or 'treatment" refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

In accordance with a first embodiment of the invention there is provided a compound of Formula I:

I

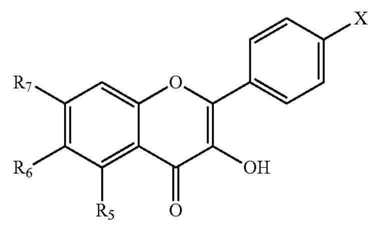

or a pharmaceutically acceptable salt or solvate thereof, wherein X is a ring deactivating group selected from —Br, —Cl, —F, —I, —$SO_2F$, —$SF_5$, —NO, —$NO_2$, —$SO_2NH_2$, —N═$CCl_2$, —$CF_3$, —$OCF_3$, —$SCF_3$, —CN, —NCS, —SCN, —$SCH_3$, —$SO_2CF_3$, —NHCN, —CHO, —$CO_2H$, —NHCHO, —$CONH_2$, —CH═NOH, —$NHCSNH_2$, —$SOCH_3$, —$OSO_2CH_3$, —$SO_2CH_3$, —$NHSO_2CH_3$, —$CF_3CF_3$, —C═CH, —NHCOCF, $CH_2CN$, —CH═$CHNO_2$, —$COCH_3$, —$SCOCH_3$, —OCOCH, —$PMe_2$, —$CO_2C_2H_5$, —$CO_2CH_3$, —$CONHCH_3$, —$SO_2C_2H_5$, —$COC_3H_7$, —$CO_2C_3H_7$, —N═$NC_6H_5$, —$SO_2C_6H_5$, —$OSO_2C_6H_5$ and —$COC_6H_5$, and —CN═$NC_6H_5$, and $R_7$, $R_6$, and $R_5$ are independently selected from H, OH, —$O(CH_2)OR_4$, and —$OR_4$, provided that at least one of $R_7$, $R_6$, and $R_5$ is OH, —$O(CH_2)OR_4$, or —$OR_4$; and $R_4$ is selected from the group consisting of $C_1$-$C_6$ alkyl, $C_1$-$C_6$ heteroalkyl, $C_1$-$C_6$ aryl, or $C_1$-$C_6$ heteroaryl.

In accordance with another embodiment of the invention there is provided a compound of Formula I:

I

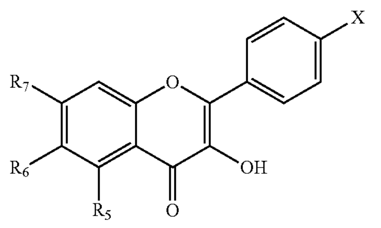

or a pharmaceutically acceptable salt or solvate thereof, wherein:

X is a ring deactivating group having a para-Hammett constant greater than zero, or wherein X is —$OCH_3$, and $R_7$, $R_6$, and $R_5$ are independently selected from H, OH, —$O(CH_2)OR_4$, and —$OR_4$, provided that at least one of $R_7$, $R_6$, and $R_5$ is OH, —$O(CH_2)OR_4$, or —$OR_4$; and $R_4$ is selected from the group consisting of $C_1$-$C_6$ alkyl, $C_1$-$C_6$ heteroalkyl, $C_1$-$C_6$ aryl, or $C_1$-$C_6$ heteroaryl, for use in a method of treating cancer in a subject, the method comprising administering a therapeutically effective amount of the compound, therapeutically acceptable salt or solvate thereof to the subject. In a particular aspect of the invention, the invention is directed the compound of Formula I, or a pharmaceutically acceptable salt or solvate thereof, is for use in a method of treating epithelial cancers in a subject.

For example, the ring deactivating group X may be selected from —Br, —Cl, —F, —I, —$SO_2F$, —$SF_5$. —NO, —$NO_2$, —$SO_2NH_2$, —N═$CCl_2$, —$CF_3$, —$OCF_3$. —$SCF_3$, —CN, —NCS, —SCN, —$SCH_3$, —$SO_2CF_3$, —NHCN, —CHO, —$CO_2H$, —NHCHO, —$CONH_2$, —CH═NOH, —$NHCSNH_2$, —$SOCH_3$, —$OSO_2CH_3$, —$SO_2CH_3$, —$NHSO_2CH_3$, —$CF_3CF_3$, —C═CH, —NHCOCF, $CH_2CN$, —CH═$CHNO_2$, —$COCH_3$, —$SCOCH_3$, —OCOCH, —$PMe_2$, —$CO_2C_2H_5$, —$CO_2CH_3$, —$CONHCH_3$, —$SO_2C_2H_5$, —$COC_3H_7$, —$CO_2C_3H_7$, —N═$NC_6H_5$, —$SO_2C_6H_5$, —$OSO_2C_6H_5$ and —$COC_6H_5$, and —CN═$NC_6H_5$.

The inventors have now for the first time found that, in most cases, a ring-deactivating group substituted at the 4'-position, as indicated by "X" in Formula I above, surprisingly enhances the cytotoxicity of these Fisetin analogues.

Figure 2:
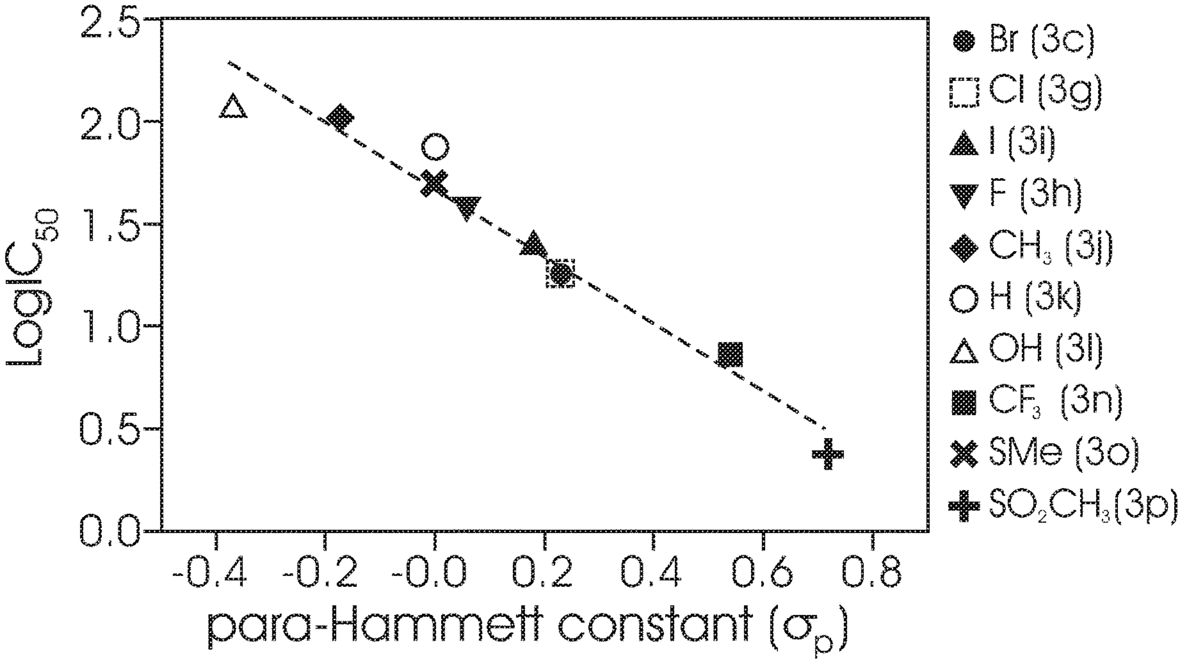
FIG. 2 shows the correlation between A549 cancer cell cytotoxicity and the para-Hammett constant of the 4'-substituent of Fisetin analogues.
Figure 3:
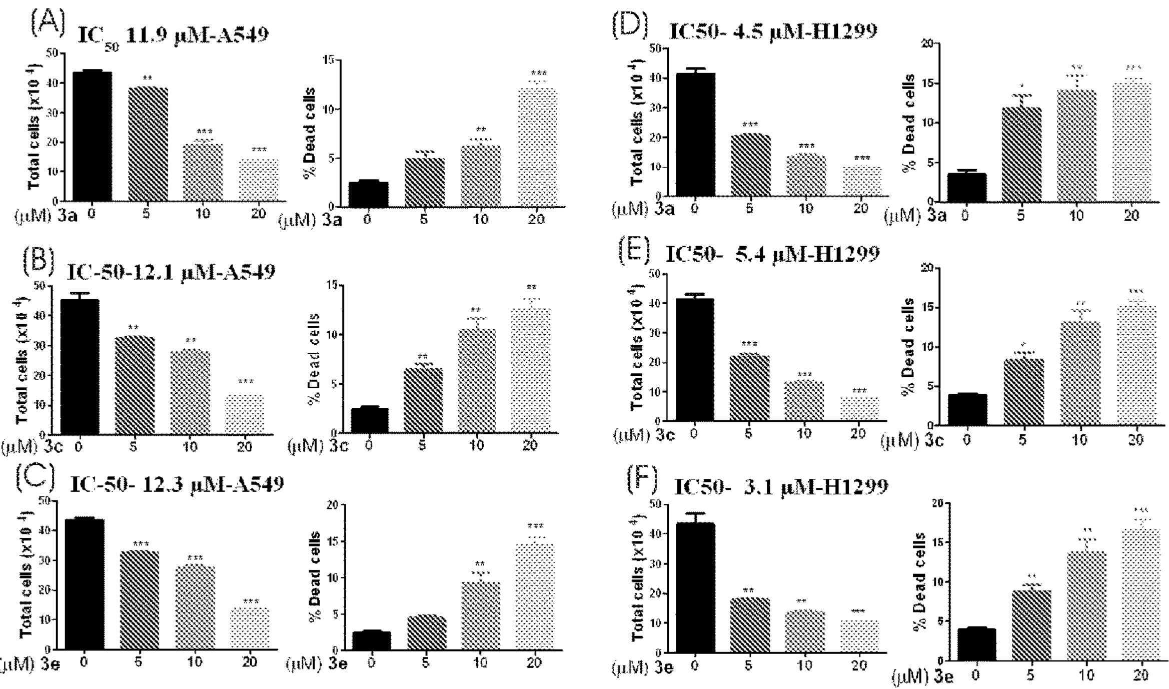
FIG. 3 shows the effect of Fisetin analogues on cell proliferation and death in human lung cancer cells.
Figure 3:
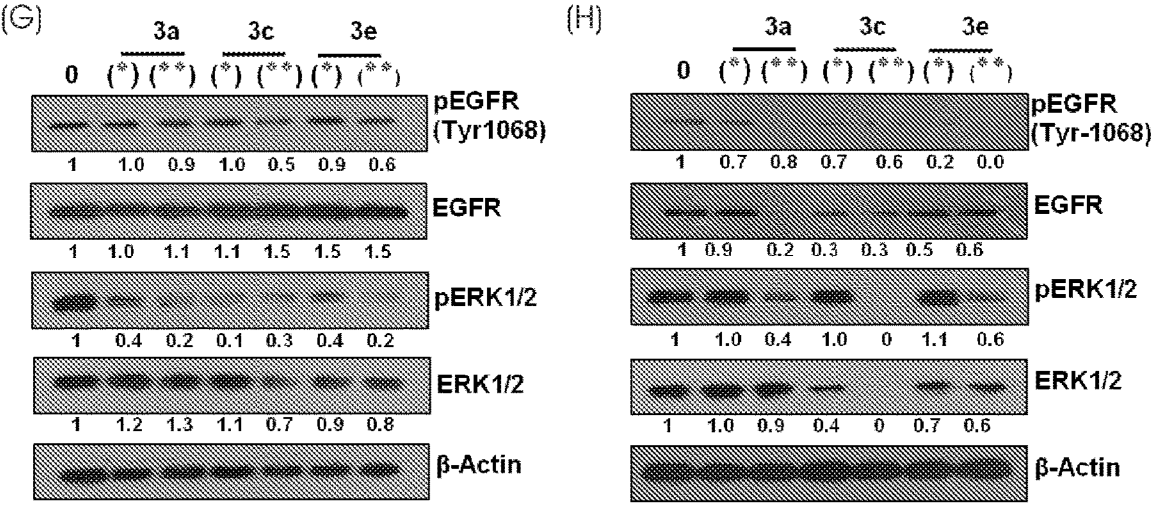

Based on the significant linear correlation which was observed between the para-Hammett constant and cytotoxicity of several 4'-substituted flavonols ($R^2$=0.935, p<0.0001, Log $IC_{50}$ (A549 cells)=−1.705×σp+1.657, FIG. 2) it is postulated that ring deactivating substituents at this 4'-position is highly likely to favour enhanced activity of these compounds. Based on the examples synthesized and tested, and the para-Hammett correlation data presented here, it is now possible for the inventors to use their knowledge and skill to predict with reasonable accuracy further examples which, based on the novel ring-deactivating group theory, have a high probability of showing favourable cytotoxicity data against epithelial cancer cells, for example lung cancer cells.

These 4'-substituted analogues of Fisetin, which are the subject of this invention, have shown to be unexpectedly advantageous over the parent Fisetin in terms of their cytotoxicity to lung cancer cell lines, in particular. For example, the 4'-substituted Br, Cl, $CF_3$, and $SO_2CH_3$ analogues (herein referred to as compounds 3c, 3g, 3n, and 3p) were found to be substantially more active against the lung cancer cell lines, A549 and/or H1299, than the parent Fisetin.

In addition, a set of three Fisetin analogues all with bromo substitution at the 4'-position, namely 3a, 3c and 3e, were all found to cause $G_2$/M cell cycle arrest, and to induce apoptosis, and to modulate the expression of apoptotic and proliferative proteins important in sustaining cancer growth in both A549 and H1299 cells.

Apoptosis pathways were modulated with increased Bax expression and reduced Bcl2 expression. Cell cycle proteins were found to be affected with an increase in p21, p27 and p53, and a decrease in cyclinB1. Cell proliferation proteins were also affected with a decrease in pERK, ERK, pAKT, AKT, STAT3 and pSTAT3. This data shows that 3a, 3c and 3e are inducing apoptosis, inhibiting cell cycle and proliferation in lung cancer cells.

The following examples are offered by way of illustration only, and not by way of limitation.

Example 1-3: Synthesis of Flavonol Analogues

In order to broaden the understanding of the structure-activity relations in Fisetin, a number of non-natural analogues of Fisetin were synthesised using established chemistry involving four consecutive steps and crystallisation purification (FIG. 1). The 4'-position was substituted for eleven different groups chosen to probe different steric and electronic effects (analogues 3c, g-p; FIG. 2). The A-ring remained as the parent Fisetin bearing a single 7-hydroxy group. All acetophenone starting materials were commercially available and were first mono-protected using a methoxymethoxy ether protecting group. The chalcones were then synthesised via a Claisen-Schmidt condensation reaction of the protected acetophenone with the para-substituted benzaldehyde to afford the corresponding protected chalcones in around 45-70% yield after crystallisation. These chalcones were then oxidatively cyclised under Algar-Flynn-Oyamada conditions ($H_2O_2$, NaOH) to produce the desired flavonols, obtained following deprotection and crystallisation in yields ranging from 50-90% yield over 2-steps.

These 4'-substituted Fisetin analogues were initially screened for cytotoxicity against the A549 lung cancer cell line following a 48 h treatment period. Cytotoxicity $IC_{50}$'s were quantified using the MTT cell proliferation assay. The compounds were not found to interfere with the assay by causing an increase in background absorbance, no correlation was found between the lipophilicity and cytotoxicity at this position, and the substituent size was also not found to be important.

Interestingly and surprisingly however, a significant linear correlation was observed between the para-Hammett constant and cytotoxicity between ten of the 4'-substituted flavonols ($R^2$=0.935, p<0.0001, Log $IC_{50}$ (A549 cells)=−1.705×σp+1.657, FIG. 2) implying that ring deactivating substituents at this position favour enhanced activity. Of the examples synthesized, the 4'-bromo, 4'-chloro, 4'-$CF_3$, and 4'-$SO_2CH_3$ derivatives were shown to be particularly active. Based on the ring deactivating theory described above, there would be a reasonable expectation of success using similar ring deactivating groups to those tested. The data shows that there is a fair expectation of activity against epithelial cancer cells where X is a ring deactivating group having a para-Hammett constant greater than zero. The more positive the number, the more active the 4'-substituted flavonol appears to be, as predicted according to the straight line equation: Log $IC_{50}$ (A549 cells)=−1.705×σp+1.657, every group being compared to H (where sigma p=0). A group deactivating relative to H has a positive number and, in contrast, activating groups are negative.

A deactivating group is able to draw electron density out of the ring thereby making the ring more electron poor (less reactive hence deactivating). This withdrawal is thought to be a combination of both inductive and resonance effects. The extent of electron withdrawal is measured on a model system using the para-substituted benzoic acid derivative. Greater electron withdrawal stabilises the conjugate base anion, which in turn lowers the $pK_a$ of the benzoic acid derivative. The Hammett constant is therefore related to the $pK_a$ of the para-substituted benzoic acid derivative. The $pK_a$ is experimentally measured and reported as a Hammett constant relative to the $pK_a$ of benzoic acid. The 4'-methoxy analogue, which is resonance donating, was the only outlier returning an enhanced activity compared to that predicted by the para-Hammett constant.

Figure 7:
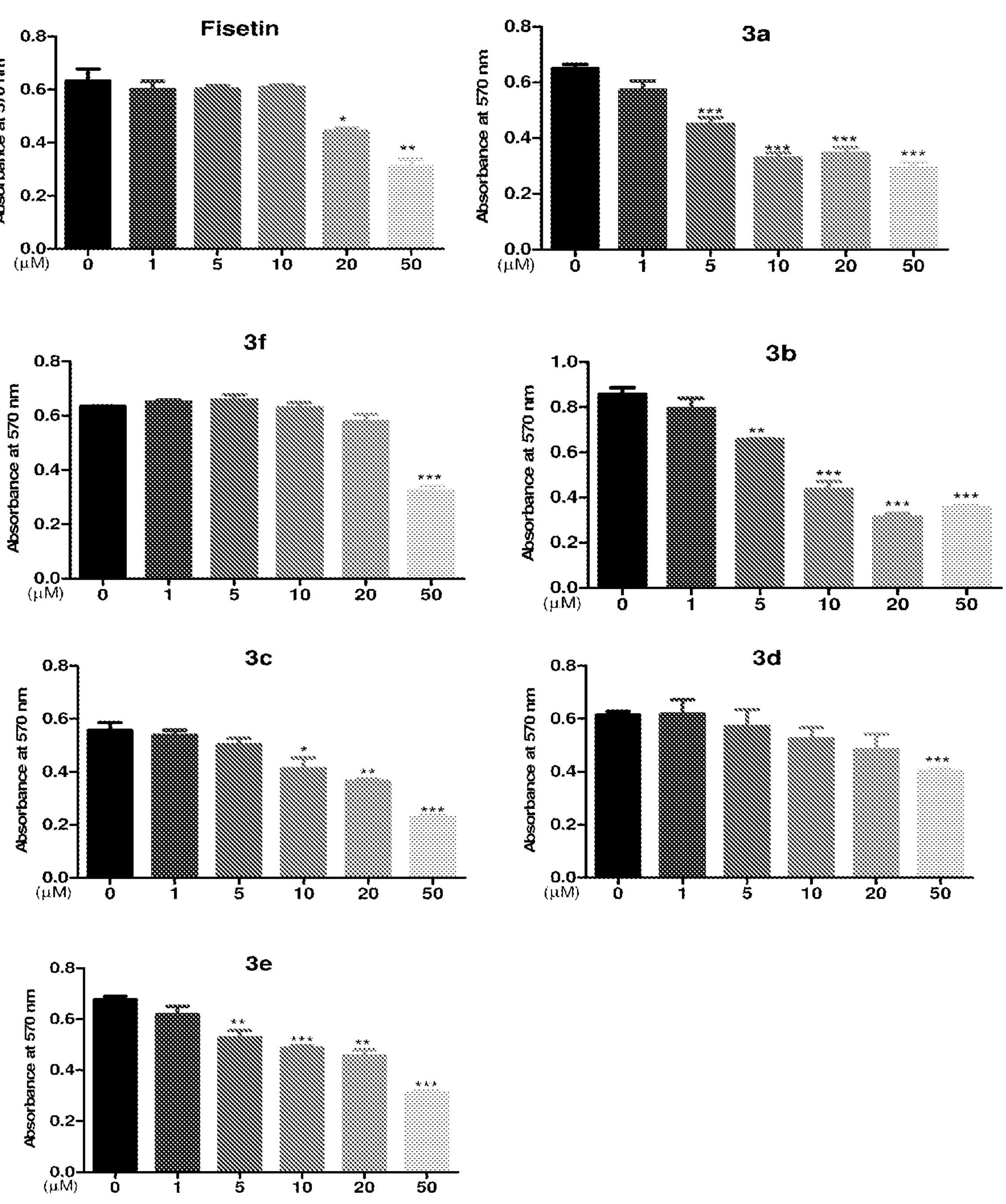
FIG. 7 shows the effect of Fisetin and its analogues on cell viability of A549 cells.
Figure 8:
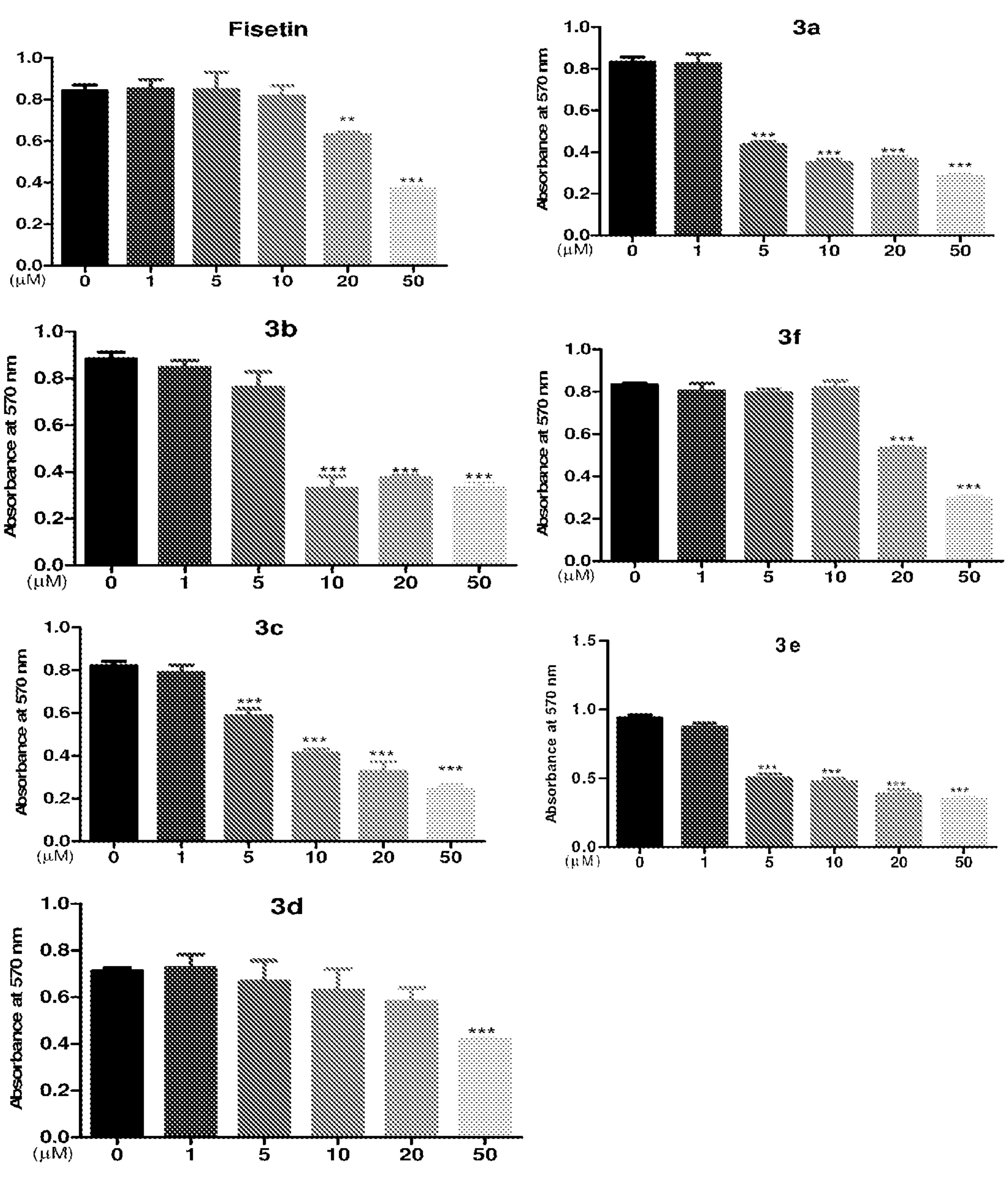
FIG. 8 shows the effect of Fisetin and its analogues on cell viability of H1299 cells.

Analogues were also synthesised to all contain Br in the B-ring 4'-position, and in which the A-ring substitution pattern alone was varied. These compounds included both the free hydroxyl group (analogues 3e, 3f), as well as some of the MOM-protected equivalents (analogues 3b, 3d), however little variation in cytotoxicity against both A549 and H1299 lung cancer cells was observed (FIGS. 7 and 8) suggesting that the A-ring substitution patterns are less important in the Fisetin analogues. Based on the strong activity of analogue 3c, it was selected together with analogues 3a and 3e for further mechanistic evaluation in lung cancer cells.

General Synthesis Methods

Unless specified otherwise, all purchased reagents were used as received without further purification. Thin layer chromatography (TLC) was used to monitor reactions using aluminium-backed plates coated with silica-gel F254. Compounds on TLC plates were observed by a combination of ultraviolet light, iodine vapour, or by spraying with a 2.5% solution of anisaldehyde in a mixture of sulfuric acid and ethanol (1:10 v/v) and then heating at 150° C. Column chromatography was performed using silica-gel 60 mesh. The melting points were determined using a Lansay International apparatus. Infrared spectra were recorded in chloroform, dichloromethane or neat on caesium chloride or sodium chloride plates on a Bruker alpha platinum-ATR diamond crystal spectrophotometer. High resolution mass spectrometry data was obtained using a Waters Synapt G2, ESI probe injected into a stream of acetonitrile, ESI positive, Cone Voltage 15. The Nuclear Magnetic Resonance (NMR) spectra were recorded at room temperature. $^1H$ and $^{13}C$ NMR spectra were recorded on Varian VNMRS 300 Liquid State NMR Spectrometer at 300 MHz for $^1H$ and 75.5 MHz for $^{13}C$; or on a Varian Unity Inova 400 spectrometer at 400 MHz for $^1H$ and 100.6 MHz for $^{13}C$ in deuteriochloroform ($CDCl_3$) or deuterodimethylsulfoxide ($CD_6SO$). Chemical shifts are quoted using residual chloroform ($\delta_H$ 7.26 in $^1H$ NMR spectra and $\delta_C$ 77.00 in $^{13}C$ NMR spectra) or residual DMSO ($\delta_H$ 2.50 in $^1H$ NMR spectra and $\delta_C$ 39.5 in $^{13}C$ NMR spectra) as an internal standard. The chemical shifts (6) in parts per million (ppm) and the coupling constants, J, were reported in Hertz (Hz). The peak patterns are indicated as follows: s, singlet; d, doublet; t, triplet; and m, multiplet. All chemicals and reagents were commercially available and were used as received unless stated otherwise.

Synthesis Route to Analogues of Fisetin

The natural flavonoids were obtained from commercial sources. The flavonol analogues were synthesised using well established chemistry, known to those skilled in the art, with four consecutive steps and crystallisation purification, as shown in FIG. 1.

All acetophenone starting materials were commercially available and were first mono-protected using a methoxymethoxy ether protecting group (step J). The flavonols were then synthesised via a Claisen-Schmidt condensation of the protected acetophenone with the para-substituted benzaldehyde to afford the corresponding protected chalcones after recrystallization (step ii). The chalcones were then oxidatively cyclised under Algar-Flynn-Oyamada conditions ($H_2O_2$, NaOH) to produce the desired flavonols (step iii), obtained following deprotection and crystallisation (step iv).

General Procedure for the Protection of Hydroxyacetophenone (Step i)

A solution of the respective dihydroxyacetophenone (1.00 g, 6.58 mmol) and oven dried potassium carbonate (27.6 g, 20.0 mmol) was stirred in dry acetone (10 mL) at room temperature for 10 min. Thereafter chloromethoxymethoxy ether (635 mg, 7.90 mmol) was added dropwise and the mixture was heated at reflux for one hour until the starting material had been consumed as observed by TLC (EtOAc: hexane 1:4). The mixture was then filtered to remove the potassium carbonate and the solvent was removed under reduced pressure. The residue was chromatographed on silica-gel using 1-12% ethyl acetate:hexane as the eluent to afford the mono-protected acetophenone as an oil.

General Procedure for the Synthesis of Chalcones (Step ii)

A stirred solution of the protected acetophenone (1a-c) (0.80 mg, 4.0 mmol) and the respective benzaldehyde (4.1 mmol) were dissolved in ethanol (10 mL) at room temperature for 10 min. Thereafter 50% aq. KOH (4 mL) was added to the solution dropwise over 5 minutes. The reaction was stirred for a further 20 h until all aldehyde had been consumed, as monitored by TLC (15% EtOAc:hexane). The solution was then cooled in an ice bath and 2M HCl (aq) was added until an acidic pH was obtained (pH 2). The precipitate was extracted into ethyl acetate (3×30 mL) which was dried over $MgSO_4$, reduced in vacuo and the residue was purified by silica gel chromatography using 70% EtOAc: hexane as the eluent. The collected chalcone was crystallised from ethanol to give yellow or orange crystals.

General Procedure for the Synthesis of Flavonols (Steps iii and iv)

A stirred solution of the protected chalcone (0.50 mmol) in 3M KOH in MeOH (8 mL) was cooled on ice to 0° C. An aqueous solution of 30% $H_2O_2$ (1.2 mL) was then added dropwise. The resulting mixture was stirred for 40 min during which it warmed to room temperature, after which the reaction was confirmed complete by TLC (30% EtOAc: hexane). The mixture was then cooled on ice and 2M HCl (aq) was added until an acidic pH was obtained. The resulting precipitate was extracted into EtOAc (3×50 mL) and the organic layer was washed with brine (1×50 mL), dried with $MgSO_4$, and concentrated under vacuum. The residue was crystallised from methanol or acetone as specified, to give the protected flavonol.

To a stirred solution of the protected flavonol (0.26 mmol) in MeOH (8 mL) at room temperature was added 3M HCl (2 mL). The reaction mixture was then heated at reflux for 3 h until the reaction was confirmed complete by TLC (25% EtOAc:hexane). The mixture was then concentrated under vacuum, diluted with water (50 mL) and the products were extracted into EtOAc (3×30 mL). The organic layer was washed with brine (50 mL) and dried over $MgSO_4$ and the solvent removed in vacuo. The residue was then crystallised from ethanol or methanol as specified. Spectroscopic details of the final flavonols are listed below.

EXPERIMENTAL RESULTS

Example 1a: 2'-Hydroxy-4'-methoxymethoxyacetophenone

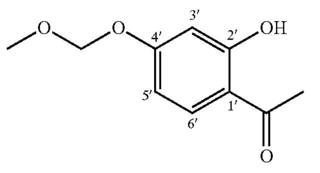

Isolated as a pale-yellow oil in 75% yield after chromatography. $\delta_H$ (400 MHz, $CDCl_3$): 12.6 (1H, s, OH), 7.64 (1H, d, J=8.0 Hz, H-6'), 6.59 (1H, d, J=2.4, H-3'), 6.54 (1H, dd, J=8.0, 2.4 Hz, H-5'), 5.20 (2H, s, $CH_2$), 3.47 (s, 3H, $ArOCH_3$), 2.56 (s, 3H, $COCH_3$); $\delta_C$ (151 MHz, $CDCl_3$) 202.7 (C═O), 164.8 (C-2), 163.5 (C-4), 132.3 (C-6), 114.7 (C-1), 108.1 (C-5), 103.7 (C-3), 93.9 ($CH_2$), 56.3 ($OCH_3$), 26.2 ($CH_3$).

Example 1b: 2'-Hydroxy-5'-methoxymethoxyacetophenone

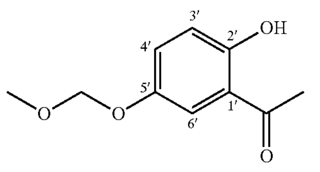

Isolated as a pale-yellow oil in 52% yield after chromatography. $\delta_H$ (400 MHz, $CDCl_3$): 11.90 (1H, s, OH), 7.36 (1H, d, J=2.9 Hz, H-6'), 7.19 (1H, dd, J=9.0, 2.9, H-4'), 6.89 (1H, d, J=9.0 Hz, H-4'), 5.10 (2H, s, $CH_2$), 3.47 (s, 3H, $OCH_3$), 2.58 (s, 3H, $COCH_3$); $\delta_C$ (151 MHz, $CDCl_3$) 204.0 (C═O), 157.5 (C-2), 149.2 (C-5), 126.4 (C-1), 119.3 and 119.1 (C-3 and C-4), 117.1 (C-6), 95.5 ($CH_2$), 55.9 ($OCH_3$), 26.7 ($CH_3$).

Example 1c: 2'-Hydroxy-6'-methoxymethoxyacetophenone

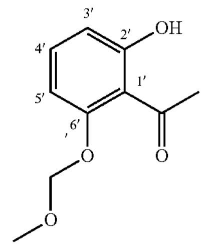

Isolated as a pale-yellow oil in 62% yield after chromatography. $\delta_H$ (300 MHz, $CDCl_3$): 13.10 (1H, s, OH), 7.33 (1H, t, J=8.4 Hz, H-4'), 6.64 (1H, dd, J=8.3, 1.0 Hz, H-3'), 6.51 (1H, dd, J=8.3, 1.0 Hz, H-5'), 5.30 (2H, s, $CH_2$), 3.54 (3H, s, $OCH_3$), 2.74 (3H, s, $COCH_3$); $\delta_C$ (75 MHz, $CDCl_3$) 205.0 (C═O), 164.4 (C-2), 158.9 (C-6), 136.1 (C-4), 111.7 (C-1), 111.6 (C-3 or C-5), 104.0 (C-3 or C-5), 94.5 ($CH_2$), 56.7 ($OCH_3$), 33.6 ($CH_3$).

Example 2a: 4-Bromo-2'-hydroxychalcone

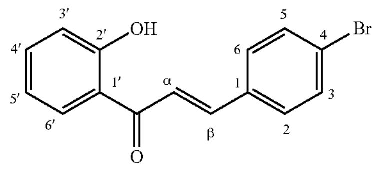 [SMILES: O=C(/C=C/c1ccc(Br)cc1)c1ccccc1O]

Starting from 2-hydroxyacetophenone (0.60 g, 4.4 mmol) was obtained as a fine yellow crystals in a 37% yield (0.49 g) after crystallisation. Melting point: 144-146° C. (Lit. 150° C., 138-139° C.). IR vmax/$cm^{-1}$: 1640, 1559, 1201, 1069, 622. $\delta_H$ (400 MHz, $CDCl_3$): 12.7 (1H, s, OH), 7.90 (1H, dd, J=8.4, 1.2 Hz, H-6'), 7.84 (1H, d, J=15.6 Hz, H-3), 7.63 (1H, d, J=15.6 Hz, H-a), 7.57 (2H, d, J=8.6 Hz, H-3 and H-5)[a], 7.52 (2H, d, J=8.6 Hz, H-2 and H-6)[a], 7.50 (1H, ddd, J=8.4, 8.4, 1.2 Hz, H-4'), 7.03 (1H, dd, J=8.4, 1.2 Hz, H-3'), 6.95 (1H, ddd, J=8.4, 8.4, 1.2 Hz, H-5'); $\delta_C$ (100.6 MHz, $CDCl_3$) 193.4, 163.6, 144.0, 136.5, 133.5, 132.3, 129.9, 129.6, 125.2, 120.7, 119.9, 118.9, 118.7. [a]Assignments may be interchangeable.

Example 2b: 4-Bromo-2'-hydroxy-4'-methoxymethoxychalcone

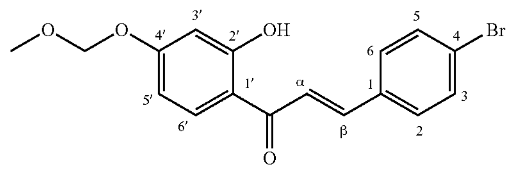 [SMILES: COCOc1ccc(C(=O)/C=C/c2ccc(Br)cc2)c(O)c1]

Starting from 1a (0.50 g, 2.5 mmol) obtained as yellow crystals in 61% yield (0.56 g) after crystallisation. Melting point: 96-98° C. IR νmax/$cm^{-1}$: 3079, 2961, 2832, 1639, 1561, 790. HRMS (m/z): Calculated: [$M+H^+$]=363.0234; Found 363.0229. $\delta_H$ (400 MHz, $CDCl_3$): 13.2 (1H, s, OH), 7.82 (1H, J=8.8 Hz, H-6'), 7.81 (1H, J=15.6 Hz, H-p3), 7.57-7.49 (5H, m, H-a, H-3, H-5, H-2, H-6)), 6.64 (1H, d, J=2.4 Hz, H-3'), 6.59 (1H, dd, J=8.8, 2.4 Hz, H-5'), 5.22 (2H, s, $OCH_2$), 3.49 (3H, s, $OCH_3$); $\delta_C$ (100.6 MHz, $CDCl_3$) 191.9, 166.4, 164.0, 143.3, 133.8, 132.4, 131.5, 130.0, 125.2, 121.0, 115.0, 108.5, 104.1, 94.2, 56.6.

Example 2c: 4-Bromo-2'-hydroxy-5'-methoxymethoxychalcone

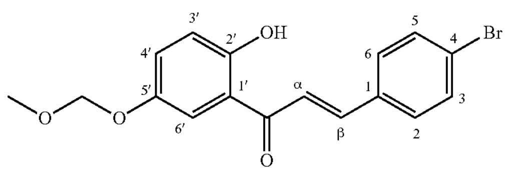 [SMILES: COCOc1ccc(O)c(C(=O)/C=C/c2ccc(Br)cc2)c1]

Starting from 1b (0.38 g, 1.9 mmol) obtained as orange crystals in 52% yield (0.37 g) after crystallisation. Melting point: 68-70° C. (Lit. 92-94° C.). IR νmax/$cm^{-1}$: 3032, 1639, 1364, 1203, 1080. HRMS (m/z): Calculated for [$M+H^+$] 363.0234; found 363.0230. $\delta_H$ (300 MHz, $CDCl_3$): 12.40 (1H, s, OH), 7.87 (1H, d, J=15.5 Hz, H-3), 7.62-7.52 (6H, m, H-a, H-6', H-2, H-3, H-5, H-6), 7.28 (1H, dd, J=9.0, 2.8 Hz, H-4'), 7.00 (1H, d, J=9.0 Hz, H-3'), 5.18 (2H, s, $OCH_2$), 3.54 (3H, s, $OCH_3$). $\delta_C$ (75.5 MHz, $CDCl_3$): 193.1, 158.9, 149.3, 144.2, 133.5, 132.3, 130.0, 126.5, 125.3, 120.6, 119.4, 116.2, 119.6, 95.6, 56.1.

Example 2d: 4-Bromo-2'-hydroxy-6'-methoxymethoxychalcone

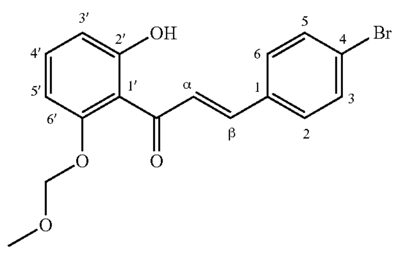 [SMILES: COCOc1cccc(O)c1C(=O)/C=C/c1ccc(Br)cc1]

Starting from 1c (0.60 g, 3.1 mmol) obtained orange crystals in 71% yield (0.79 g) after crystallisation. Melting point: 64-66° C. IR νmax/$cm^{-1}$: 3047, 1630, 1349, 120, 1043, HRMS (m/z): Calculated for [$M+H^+$] 363.0234; found 363.0225. $\delta_H$ (300 MHz, $CDCl_3$): 12.82 (1H, s, OH), 7.90 (1H, d, J=15.5 Hz, H-3), 7.75 (1H, d, J=15.5 Hz, H-a), 7.48-7.59 (4H, m, H-2, H-3, H-5, H-6), 7.37 (1H, app t, dd, J=8.4 Hz, H-4'), 6.69 (1H, dd, J=8.4, 1.0 Hz, H-3'), 6.62 (1H, dd, J=8.4, 1.0 Hz, H-5'), 5.32 (2H, s, $OCH_2$), 3.54 (3H, s, $OCH_3$). $\delta_C$ (75.5 MHz, $CDCl_3$): 194.2, 164.5, 158.3, 141.4, 136.0, 134.2, 132.2, 129.7, 128.1, 124.6, 112.6, 111.9, 104.8, 95.2, 56.9.

Example 2e: 4-Chloro-2'-hydroxy-4'-methoxymethoxychalcone

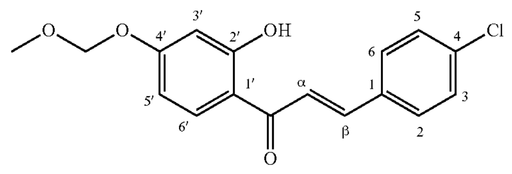 [SMILES: COCOc1ccc(C(=O)/C=C/c2ccc(Cl)cc2)c(O)c1]

Starting from 1a (0.50 g, 2.5 mmol) obtained as yellow crystals in 50% yield (0.41 g) after crystallisation. Melting point: 118-120° C. IR νmax/$cm^{-1}$: 3038, 2966, 2832, 1640, 1561, 791. HRMS (m/z): Calculated for [$M+H^+$] 319.0739; found 319.0736. $\delta_H$(300 MHz, $CDCl_3$): 13.2 (1H, s, OH), 7.83 (1H, d, J=15.4 Hz, H-3), 7.83 (1H, J=8.8 Hz, H-6'), 7.58 (2H, d, J=8.4 Hz, H-3 and H-5)[a], 7.54 (1H, d, J=15.4 Hz, H-a), 7.40 (2H, d, J=8.4 Hz, H-2 and H-6)[a], 6.65 (1H, d, J=2.4 Hz, H-3'), 6.59 (1H, d, J=8.8, 2.4 Hz, H-5'), 5.22 (2H, s, $OCH_2$), 3.49 (3H, s, $OCH_3$); $\delta_C$ (75.3 MHz, $CDCl_3$) 191.9, 166.4, 163.9, 143.2, 136.8, 133.4, 131.4, 129.8, 129.4, 120.9, 115.0, 108.5, 104.1, 94.2, 56.6. [a]Assignments may be interchangeable.

Example 2f: 4-Fluoro-2'-hydroxy-4'-methoxymethoxychalcone

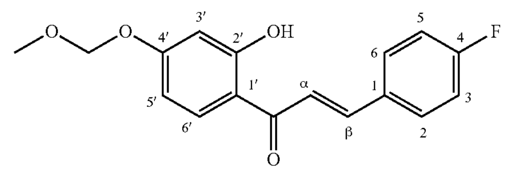 [SMILES: COCOc1ccc(C(=O)/C=C/c2ccc(F)cc2)c(O)c1]

Starting from 1a (0.62 g, 3.2 mmol) obtained as bright yellow crystals in 44% yield (0.42 g) after crystallisation. Melting point: 61-64° C. IR νmax/$cm^{-1}$: 2915, 1636, 1600, 1359, 980. HRMS (m/z): Calculated for [$M+H^+$] 303.1034, found 303.1030. $\delta_H$ (400 MHz, $CDCl_3$): 13.2 (1H, s, OH), 7.87 (1H, d, J=15.5 Hz, H-3), 7.86 (1H, d, J=9.0 Hz, H-6'), 7.64 (2H, m, H-3 and H-5)[a], 7.51 (1H, m, J=15.5 Hz, H-a), 7.14 (2H, m, H-2 and H-6)[a], 6.66 (1H, d, J=2.4 Hz, H-3'), 6.60 (1H, dd, J=9.0, 2.4 Hz, H5'), 5.25 (2H, s, $OCH_2$), 3.51 (3H, s, $OCH_3$). $\delta_C$ (100.6 MHz, $CDCl_3$): 191.8, 166.2, 164.1 (d, J=250 Hz), 163.7, 143.3, 131.3, 131.0 (d, J=3.4 Hz), 130.4 (d, J=8.5 Hz), 120.0 (d, J=2.3 Hz), 116.2 (d, J=21.8 Hz), 114.9, 108.3, 104.0, 94.0, 56.4. [a] Assignments may be interchangeable.

Example 2g: 4-Iodo-2'-hydroxy-4'-methoxymethoxychalcone

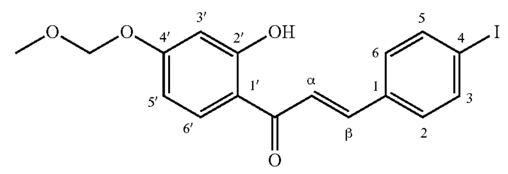 [SMILES: COCOc1ccc(C(=O)/C=C/c2ccc(I)cc2)c(O)c1]

Starting from 1a (0.36 g, 1.9 mmol) obtained as yellow crystals in 45% yield (0.38 g) after crystallisation. Melting point: 130-136° C. IR νmax/$cm^{-1}$: 2937, 2837, 1640, 1233, 1139, 974, 793. HRMS (m/z): Calculated for $[M+H^+]$ 411.0093; found 411.0089. $\delta_H$ (600 MHz, $CDCl_3$): 13.2 (1H, s, OH), 7.80 (1H, d, J=8.6 Hz, H-6'), 7.76 (1H, d, J=15.6 Hz, H-3), 7.74 (2H, d, J=7.8 Hz, H-3 and H-5)[a], 7.54 (1H, d, J=15.6 Hz, H-a), 7.34 (2H, d, J=7.8 Hz, H-2 and H-6)[a], 6.62 (1H, d J=2.4 Hz, H-3'), 6.56 (1H, dd, J=8.6, 2.4 Hz, H-5'), 5.20 (2H, s, $OCH_2$), 3.46 (3H, s, $OCH_3$); $\delta_C$ (100.6 MHz, $CDCl_3$) 191.7, 166.3, 163.8, 143.3, 138.2, 134.2, 131.3, 129.9, 120.9, 114.9, 108.4, 104.0, 97.1, 94.1, 56.5. [a]Assignments may be interchangeable.

Example 2h: 4-Methyl-2'-hydroxy-4'-methoxymethoxychalcone

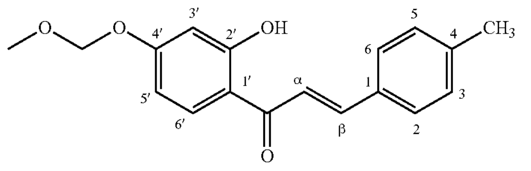

Starting from 1a (0.35 g, 1.8 mmol) obtained as bright yellow crystals in 52% yield (0.28 g) after crystallisation. Melting point: 92-96° C. IR νmax/$cm^{-1}$: 2911, 1631, 1605, 1357, 981, 795. HRMS (m/z): Calculated for $[M+H^+]$ 299.1285; found 299.1286. $\delta_H$(300 MHz, $CDCl_3$): 13.2 (1H, s, OH), 7.88 (1H, d, J=15.6 Hz, H-3), 7.85 (1H, d, J=9.0 Hz, H-6'), 7.55 (2H, d, J=8.0 Hz, H-2 and H-6)[a], 7.54 (1H, d, J=15.6 Hz, H-a), 7.24 (2H, d, J=8.0 Hz, H-3 and H-5)[a], 6.64 (1H, d, J=2.4 Hz, H-3'), 6.59 (1H, dd, J=9.0, 2.4 Hz, H-5'), 5.22 (2H, s, $OCH_2$), 3.48 (3H, s, $OCH_3$), 2.40 (3H, s, $CH_3$); $\delta_C$ (75.5 MHz, $CDCl_3$) 192.1, 166.2, 163.6, 144.7, 141.3, 132.0, 131.3, 129.7, 128.6, 119.2, 115.0, 108.2, 104.0, 94.0, 56.4, 21.6. [a]Assignments may be interchangeable.

Example 2i: 2'-Hydroxy-4,4'-dimethoxymethoxy-chalcone

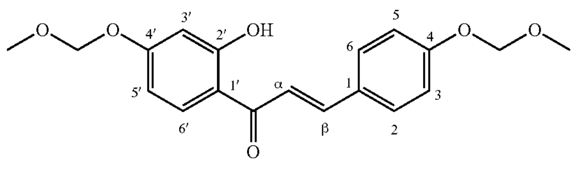

Starting from 1a (0.57 g, 2.9 mmol) obtained as yellow crystals in 42% yield (0.42 g) after crystallisation. Melting point: 57-59° C. IR νmax/$cm^{-1}$: 2917, 1640, 1600, 1339, 974. HRMS (m/z): Calculated for $[M+H^+]$ 345.1338; found 345.1328. $\delta_H$ (300 MHz, $CDCl_3$): 13.37 (1H, s, OH), 7.89 (1H, d, J=15.3 Hz, H-3), 7.88 (1H, d, J=9.0 Hz, H-6'), 7.63 (2H, d, J=8.8 Hz, H-2 and H-6)[a], 7.50 (1H, d, J=15.3 Hz, H-a), 7.11 (2H, d, J=8.8 Hz, H-3 and H-5)[a], 6.67 (1H, J=2.4 Hz, H-3'), 6.61 (1H, J=9.0, 2.4 Hz, H-5'), 5.25 (4H, s, 2×$OCH_2$), 3.52 (3H, s, $OCH_3$), 3.51 (3H, s, $OCH_3$); $\delta_C$ (75.5 MHz, $CDCl_3$) 192.0, 166.1, 163.5, 159.4, 144.3, 131.2, 130.3, 128.5, 118.2, 116.5, 115.0, 108.1, 104.0, 94.2, 94.0, 56.4, 56.2. [a]Assignments may be interchangeable.

Example 2j: 4-Methoxy-2'-hydroxy-4'-methoxymethoxychalcone

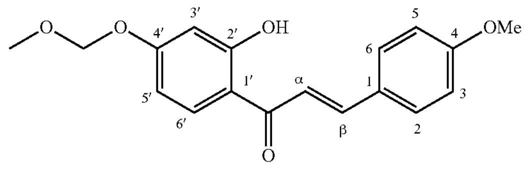 [SMILES: COCOc1ccc(C(=O)/C=C/c2ccc(OC)cc2)c(O)c1]

Starting from 1a (0.45 g, 2.3 mmol) obtained as yellow crystals in 53% yield (0.38 mg) after crystallisation. Melting point: 81-84° C. IR νmax/$cm^{-1}$: 3092, 2902, 1605, 1567, 1508, 1425, 1361. HRMS (m/z): Calculated for $[M+H^+]$ 315.1234; found 315.1231. $\delta_H$(300 MHz, $CDCl_3$): 13.42 (1H, s, OH), 7.82 (1H, d, J=15.5 Hz, H-3), 7.81 (1H, d, J=9.0 Hz, H-6'), 7.56 (2H, d, J=8.7 Hz, H-2 and H-6)[a], 7.41 (1H, d, J=15.5 Hz, H-a), 6.90 (2H, d, J=8.7 Hz, H-3 and H-5)[a], 6.62 (1H, J=2.4 Hz, H-3'), 6.56 (1H, J=9.0, 2.4 Hz, H-5'), 5.19 (2H, s, $OCH_2$), 3.81 (3H, s, $ArOCH_3$), 3.47 (3H, s, $OCH_3$); $\delta_C$ (75.5 MHz, $CDCl_3$) 192.0, 166.1, 163.5, 161.8, 144.5, 131.2, 130.4, 127.4, 117.6, 115.0, 114.5, 108.1, 103.9, 94.0, 56.4, 55.4. [a]Assignments may be interchangeable.

Example 2k: 2'-hydroxy-4'-methoxymethoxychalcone

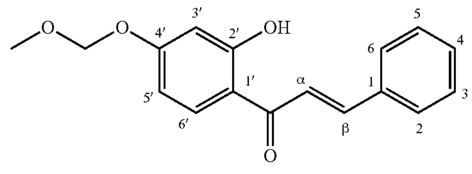 [SMILES: COCOc1ccc(C(=O)/C=C/c2ccccc2)c(O)c1]

Starting from 1a (0.27 g, 1.4 mmol) obtained as yellow crystals in 56% yield (0.22 g) after crystallisation. Melting point: 62-66° C. IR νmax/$cm^{-1}$: 2964, 2828, 1633, 981, 797. HRMS (m/z): Calculated for $[M+H^+]$ 285.1127; found 285.1125. $\delta_H$ (300 MHz, $CDCl_3$): 13.29 (1H, s, OH), 7.91 (1H, d, J=15.5 Hz, H-3), 7.86 (1H, d, J=9.0 Hz, H-6'), 7.66-7.70 (2H, m, Ar—H), 7.60 (1H, d, J=15.5 Hz, H-a), 7.43-7.48 (3H, m, Ar—H), 6.67 (1H, d, J=2.4 Hz, H-3'), 6.62 (1H, dd, J=9.0, 2.4 Hz, H-5'), 5.25 (2H, s, $OCH_2$), 3.51 (3H, s, $OCH_3$); $\delta_C$ (75.5 MHz, $CDCl_3$) 192.0, 166.2, 163.7, 144.6, 134.7, 131.4, 130.7, 129.0, 128.6, 120.2, 114.9, 108.3, 104.0, 94.0, 56.4.

Example 3a: 4'-Bromo-3-hydroxyflavone (3a)

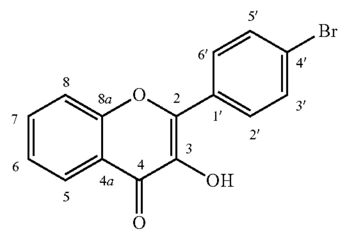 [SMILES: O=c1c(O)c(-c2ccc(Br)cc2)oc2ccccc12]

Starting from 0.080 g (0.26 mmol) was obtained as a yellow solid in 62% (0.052 g) yield after chromatography using 30-40% EtOAc:hexane as the eluent. Melting point: 200-202. (Lit. 197-199° C.). IR νmax·$cm^{-1}$ 3267, 2919, 1601, 1567, 1346, 1212, 1007, HRMS (m/z): Calculated for [$M+H^+$] 316.9813; found 316.9813. $\delta_H$ (400 MHz, DMSO-$d_6$): 9.85 (1H, s, OH), 8.18 (2H, d, J=8.6 Hz, H-3' and H-5'), 8.12 (1H, dd, J=8.0, 1.6 Hz), 7.74-7.84 (2H, m), 7.78 (2H, d, J=8.6 Hz, H-2' and H-6'), 7.48 (1H, t, J=8.0 Hz). $\delta_C$ (100.6 MHz, DMSO-$d_6$): 173.5, 155.0, 144.5, 139.9, 134.3, 132.1, 131.1, 130.0, 125.3, 125.1, 123.8, 121.8, 118.9.

Example 3b: 4'-Bromo-3-hydroxy-7-methoxymethoxyflavone (3b)

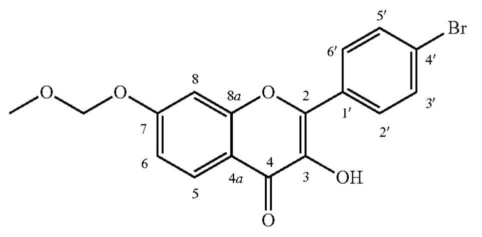 [SMILES: COCOc1ccc2c(=O)c(O)c(-c3ccc(Br)cc3)oc2c1]

Starting from 0.180 g (0.50 mmol) was obtained as a pale-yellow solid in a 60% yield (0.113 g) after crystallisation from acetone. Melting point: 180-182° C. IR νmax·$cm^{-1}$: 3236, 2919, 1604, 775, 702, 479. HRMS (m/z): Calculated for [$M+H^+$] 377.0024; found 377.0022. $\delta_H$ (600 MHz, DMSO-$d_6$): 9.74 (1H, s, OH), 8.17 (2H, d, J=9.0 Hz, H-3' and H-5'), 8.03 (1H, d, J=8.4 Hz, H-5), 7.77 (2H, d, J=9.0 Hz, H-2' and H-6'), 7.34 (1H, d, J=2.4 Hz, H-8), 7.13 (1H, dd, J=8.4, 2.4 Hz, H-6), 5.37 (2H, s, $CH_2$), 3.43 (3H, s, $CH_3$). $\delta_C$ (151 MHz, DMSO-$d_6$): 172.8, 161.4, 156.4, 144.0, 139.5, 132.0, 131.0, 129.7, 126.8, 123.5, 116.3, 115.8, 103.3, 94.5, 56.5.

Example 3c: 4'-Bromo-3,7-dihydroxyflavone (3c)

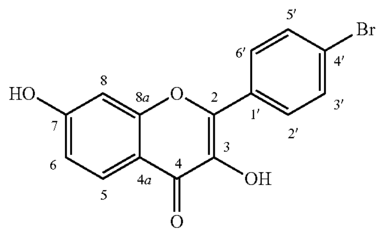 [SMILES: O=c1c(O)c(-c2ccc(Br)cc2)oc2cc(O)ccc12]

Starting from 0.10 g (0.28 mmol) was obtained as a pale-yellow solid in 65% yield (0.060 g) after crystallisation from methanol. Melting point: 292-296° C. with decomposition. IR νmax·$cm^{-1}$: 3334, 3083, 1629, 1571, 1393, 1228, 1014. HRMS (m/z): Calculated for [$M+H^+$] 332.9764; found 332.9767. $\delta_H$ (300 MHz, DMSO-$d_6$): 10.82 (1H, s, OH), 9.59 (1H, s, OH), 8.13 (2H, d, J=8.7 Hz, H-2' and H-6'), 7.95 (1H, d, J=8.7 Hz, H-5), 7.75 (2H, d, J=8.7 Hz, H-3' and H-5'), 6.98-6.90 (2H, m, H-6 and H-8). $\delta_C$ (75.5 MHz, DMSO-$d_6$): 172.8, 163.1, 156.9, 143.4, 139.3, 132.0, 131.2, 129.7, 127.1, 123.3, 115.5, 114.7, 102.5.

Example 3d: 4'-Bromo-3-hydroxy-6-methoxymethoxyflavone (3d)

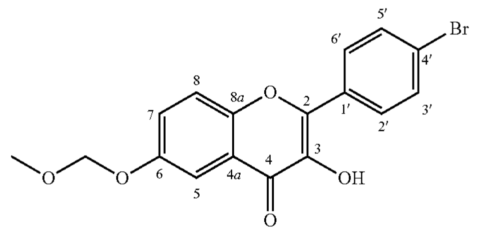 [SMILES: COCOc1ccc2oc(-c3ccc(Br)cc3)c(O)c(=O)c2c1]

Starting from 0.180 g (0.50 mmol) was obtained as a pale-yellow solid in 72% (0.135 g) yield after crystallisation from methanol. Melting point: 168-170° C. IR νmax·$cm^{-1}$: 3298, 3047, 1621, 1581, 1389, 1214, 1096, 1009, HRMS (m/z): Calculated for [$M+H^+$] 377.0024; found 377.0028. $\delta_H$ (600 MHz, DMSO-$d_6$): 9.75 (1H, s, OH), 8.12 (2H, d, J=8.4 Hz, H-3' and H-5'), 7.72 (2H, d, J=8.4 Hz, H-6' and H-2'), 7.69 (1H, d, J=9.0 Hz, H-8), 7.56 (1H, s, H-5), 7.43 (1H, d, J=9.0 Hz, H-7), 5.26 (2H, s, $CH_2$), 3.37 (3H, s, $CH_3$). $\delta_C$ (151 MHz, DMSO-$d_6$): 173.0, 153.8, 150.4, 144.4, 139.4, 132.0, 131.0, 129.9, 125.0, 123.7, 122.3, 120.5, 108.1, 94.7, 56.2.

Example 3e: 4'-Bromo-3,6-dihydroxyflavone (3e)

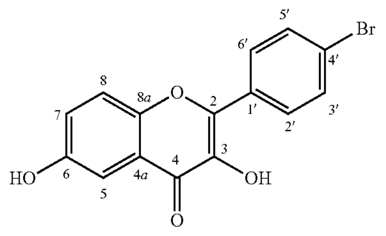 [SMILES: O=c1c(O)c(-c2ccc(Br)cc2)oc2ccc(O)cc12]

Starting from 0.096 g (0.27 mmol) was obtained as a pale-yellow solid in 52% yield (0.046 g) after crystallisation from methanol. Melting point >260° C. with decomposition. IR νmax·$cm^{-1}$: 3355, 1630, 1581, 1371, 1231, 1012. HRMS (m/z): Calculated for [$M+H^+$] 332.9764; found 332.9761. $\delta_H$ (400 MHz, DMSO-$d_6$): 9.95 (1H, s, OH), 9.62 (1H, s, OH), 8.13 (2H, d, J=8.4 Hz, H-3' and H-5'), 7.74 (2H, d, J=8.4 Hz, H-2' and H-6'), 7.61 (1H, d, J=9.2 Hz, H-8), 7.33 (1H, d, J=2.8 Hz, H-5), 7.24 (1H, dd, J=9.2, 2.8 Hz, H-7). $\delta_C$ (100.6 MHz, DMSO-$d_6$): 173.1, 154.6, 149.0, 144.2, 139.1, 132.0, 131.2, 129.9, 123.9, 123.6, 122.5, 120.2, 107.2.

Example 3f: 4'-Bromo-3,5-dihydroxyflavone (3f)

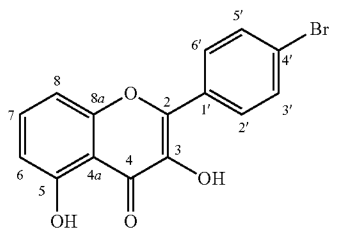 [SMILES: O=c1c(O)c(-c2ccc(Br)cc2)oc2cccc(O)c12]

Starting from 0.156 g (0.43 mmol) was obtained as a yellow-orange solid in 49% yield (0.070 g) after crystallisation from methanol. Melting point: 240-243° C. with decomposition. IR νmax·$cm^{-1}$: 3353, 3108, 1741, 1604, 1579, 1230, 597. HRMS (m/z): Calculated for $[M+H^+]$ 332.9764; found 332.9753. $\delta_H$ (600 MHz, DMSO-$d_6$): 11.21 (1H, s, OH), 7.89 (2H, d, J=8.7 Hz, H-3' and H-5'), 7.70 (2H, d, J=8.7 Hz, H-2' and H-6'), 7.55 (1H, dd, J=7.8, 7.8 Hz, H-7), 6.86 (1H, d, J=7.8 Hz, H-8), 6.76 (1H, s, OH), 6.65 (1H, d, J=7.8 Hz, H-6). $\delta_C$ (151 MHz, DMSO-$d_6$): 181.7, 166.4, 157.7, 147.3, 139.3, 133.1, 132.4, 131.9, 123.4, 111.3, 109.3, 109.0, 102.8.

Example 3g: 4'-Chloro-3,7-dihydroxyflavone (3g)

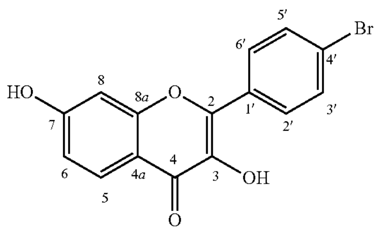 [SMILES: O=c1c(O)c(-c2ccc(Br)cc2)oc2cc(O)ccc12]

Starting from 0.094 g (0.29 mmol) was obtained as a pale-yellow solid in 85% yield (0.072 g) after crystallisation from methanol. Melting point: 283-290° C. IR νmax·$cm^{-1}$: 1640, 1561, 1489, 1317, 1275, 791. HRMS (m/z): Calculated for $[M+H^+]$ 289.0269; found 289.0263. $\delta_H$ (400 MHz, DMSO-$d_6$): 10.91 (1H, s, OH), 9.58 (1H, s, OH), 8.20 (2H, d, J=8.8 Hz, H-2' and H-6'), 7.94 (1H, d, J=8.4 Hz, H-5), 7.62 (2H, d, J=8.8 Hz, H-3' and H-5'), 6.98 (1H, d, J=2.2 Hz, H-8), 6.94 (1H, dd, J=8.4, 2.2 Hz, H-6). $\delta_C$ (100.6 MHz, DMSO-$d_6$): 172.8, 163.3, 156.9, 143.3, 139.2, 134.4, 130.8, 129.5, 129.0, 127.0, 115.5, 114.6, 102.4.

Example 3h: 4'-Fluoro-3,7-dihydroxyflavone (3h)

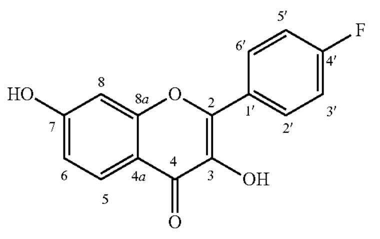 [SMILES: O=c1c(O)c(-c2ccc(F)cc2)oc2cc(O)ccc12]

Starting from 0.085 g (0.28 mmol) was obtained as a pale-yellow solid in 73% yield (0.056 g) after crystallisation from methanol. Melting point: 164-166° C. IR νmax·$cm^{-1}$: 1638, 1561, 1141, 795, 649. HRMS (m/z): Calculated for $[M+H^+]$ 273.0565 found 273.0559. $\delta_H$ (400 MHz, DMSO-$d_6$): 10.95 (1H, s, OH), 9.42 (1H, s, OH), 8.22 (2H, dd, J=9.0, 2.0 Hz, H-2' and H-6'), 7.92 (1H, d, J=8.4 Hz, H-5), 7.37 (2H, dd, J=9.0, 9.0 Hz, H-3' and H-5'), 6.99 (1H, d, J=2.4 Hz, H-8), 6.93 (1H, dd, J=8.8, 2.4 Hz, H-6). $\delta_C$ (100.6 MHz, DMSO-$d_6$): 172.7, 163.6 (d, J=248 Hz), 163.2, 156.9, 143.8, 138.7, 130.3 (d, J=8.7 Hz), 128.5 (d, J=3.1 Hz), 126.9, 116.0 (d, J=21.6 Hz), 115.5, 114.6, 102.4.

Example 3i: 4'-Iodo-3,7-dihydroxyflavone (3i)

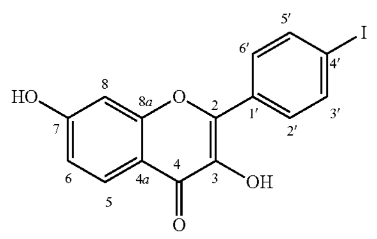 [SMILES: O=c1c(O)c(-c2ccc(I)cc2)oc2cc(O)ccc12]

Starting from 0.110 g (0.27 mmol) was obtained as a pale-yellow solid in 89% yield (0.091 g) after crystallisation from methanol. Melting point >260° C. IR νmax·$cm^{-1}$: 3345, 2616, 1627, 1561, 1275, 768, 556. HRMS (m/z): Calculated for $[M+H^+]$ 380.9626; found 380.9622. $\delta_H$ (400 MHz, DMSO-$d_6$): 11.03 (1H, s, OH), 9.52 (1H, s, OH), 7.97-7.88 (5H, m, H-2', H-3', H-5', H-6', H-5), 6.98 (1H, d, J=2.0 Hz, H-8), 6.93 (1H, dd, J=8.8, 2.0 Hz, H-6). $\delta_C$ (150 MHz, DMSO-$d_6$): 175.4, 165.8, 159.6, 146.2, 141.9, 140.5, 134.1, 132.2, 129.7, 118.1, 117.3, 105.1, 99.6.

Example 3j: 4'-Methyl-3,7-dihydroxyflavone (3j)

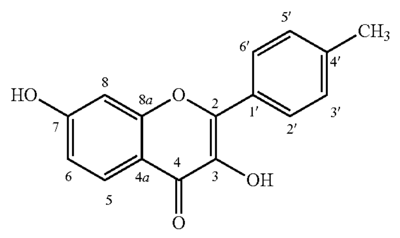 [SMILES: Cc1ccc(-c2oc3cc(O)ccc3c(=O)c2O)cc1]

Starting from 0.090 g (0.30 mmol) was obtained as a pale-yellow solid in 54% yield (0.044 g) after crystallisation from methanol. Melting point: 276-282° C. IR νmax·$cm^{-1}$: 3343, 1625, 1545, 1281, 816. HRMS (m/z): Calculated for $[M+H^+]$ 269.0816; found 269.0813. $\delta_H$ (400 MHz, DMSO-$d_6$): 10.92 (1H, s, OH), 9.25 (1H, s, OH), 8.06 (1H, d, J=8.6 Hz, H-5), 7.91 (2H, d, J=8.6 Hz, H-2' and H-6'), 7.33 (2H, d, J=8.6 Hz, H-3' and H-5'), 6.96 (1H, J=2.4 Hz, H-8), 6.92 (1H, d, J=8.6, 2.4 Hz, H-6), 2.36 (3H, s, $CH_3$). $\delta_C$ (100.6 MHz, DMSO-$d_6$): 172.7, 163.1, 156.9, 144.8, 139.8, 138.6, 129.6, 129.2, 127.7, 126.9, 115.4, 114.6, 102.4, 21.5.

Example 3k: 3,7-dihydroxyflavone (3k)

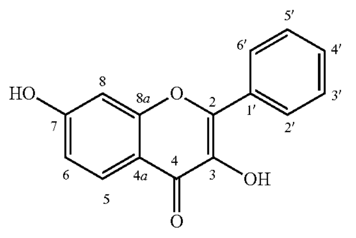 [SMILES: O=c1c(O)c(-c2ccccc2)oc2cc(O)ccc12]

Starting from 0.105 g (0.37 mmol) was obtained as a pale-yellow solid in 86% yield (0.081 g) after crystallisation from methanol. Melting point: 252-255° C. (Lit. 258-260). IR νmax·cm[1]: 3421, 1625, 1605, 1563, 1425, 770. HRMS (m/z): Calculated for [M+H$^+$] 255.0657; found 255.0659. $\delta_H$ (400 MHz, DMSO-$d_6$): 10.94 (1H, s, OH), 9.37 (1H, s, OH), 8.15 (2H, dd, J=7.2, 1.2 Hz, H-2' and H-6'), 7.92 (1H, d, J=4.8 Hz, H-5), 7.56-7.50 (2H, m, H-3' and H-5'), 7.49-7.43 (1H, m, H-4'), 6.99 (1H, d, J=2.2 Hz, H-8), 2.94 (1H, dd, J=8.8, 2.2 Hz, H-6). $\delta_C$ (100.6 MHz, DMSO-$d_6$): 172.8, 163.2, 157.0, 144.5, 138.9, 131.9, 129.9, 128.9, 127.8, 126.9, 115.4, 114.6, 102.4.

Example 3l: 3,4',7-trihydroxyflavone (3l)

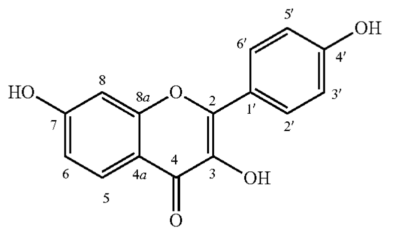

Starting from 0.085 g (0.025 mmol) was obtained as a pale-yellow solid in 85% yield (0.057 g) after crystallisation from methanol. Melting point: 278-280° C. with decomposition (Lit. 223-224° C.). IR νmax·cm$^{-1}$: 3477, 1625, 1543, 1271, 1172, 880, 766. HRMS (m/z): Calculated for [M+H$^+$] 271.0606; found 271.0605. $\delta_H$ (400 MHz, DMSO-$d_6$): 10.82 (1H, s, OH), 10.14 (1H, s, OH), 9.01 (1H, s, OH-7), 8.02 (2H, d, J=9.2 Hz, H-2' and H-6'), 7.89 (1H, d, J=8.8 Hz, H-5), 6.94 (2H, d, J=2.4 Hz, H-8), 6.92 (2H, d, J=9.2 Hz, H-3' and H-5'), 6.90 (1H, dd, J=8.8, 2.4 Hz, H-6). $\delta_C$ (100.6 MHz, DMSO-$d_6$): 172.4, 162.9, 159.2, 156.8, 145.4, 137.5, 129.6, 126.8, 122.6, 115.8, 115.2, 114.6, 102.4.

Example 3m: 4'-Methoxy-3,7-dihydroxyflavone (3m)

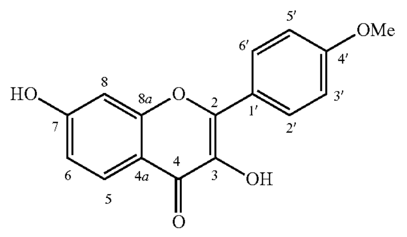 [SMILES: COc1ccc(-c2oc3cc(O)ccc3c(=O)c2O)cc1]

Starting from 0.070 g (0.022 mmol) was obtained as a pale-yellow solid in 95% yield (0.060 g) after silica gel chromatography using 40-60% EtOAc:hexane as the eluent. Melting point: 246-248° C. with decomposition (Lit. 270-272° C.). IR νmax·cm$^{-1}$: 3339, 3037, 2921, 1633, 1576, 1427, 1410, 1254. HRMS (m/z): Calculated for [M+H$^+$] 285.0765; found 285.0757. $\delta_H$ (400 MHz, DMSO-$d_6$): 10.75 (1H, s, OH), 9.17 (1H, s, OH), 8.14 (2H, d, J=9.0 Hz, H-2' and H-6'), 7.94 (1H, d, J=8.6 Hz, H-5), 7.10 (2H, d, J=9.0 Hz, H-3' and H-5'), 6.95 (1H, d, J=2.0 Hz, H-8), 6.91 (1H, dd, J=8.6, 2.0 Hz, H-6), 3.83 (3H, s, $OCH_3$). $\delta_C$ (100.6 MHz, DMSO-$d_6$): 172.5, 162.9, 160.6, 156.8, 145.0, 137.9, 129.5, 126.9, 124.2, 115.3, 114.7, 114.4, 102.4, 55.7.

Example 3n: 4'-Trifluoromethyl-3,7-dihydroxyflavone (3n)

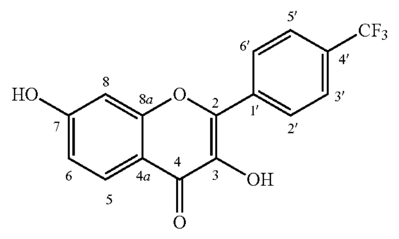 [SMILES: O=c1c(O)c(-c2ccc(C(F)(F)F)cc2)oc2cc(O)ccc12]

Starting from 0.060 g (0.164 mmol) was obtained as a pale-yellow solid in a 71% yield (0.037 g) after crystallisation from methanol. Melting point: 266-270° C. IR νmax·cm$^{-1}$: 3360, 3052, 1565, 1518, 1456, 1320, 1283, 1167, 1069, 840, 774. HRMS (m/z): Calculated for [M+H$^+$] 323.0533; found 323.0536. $\delta_H$ (600 MHz, DMSO-$d_6$): 10.26 (s, 1H), 8.38 (d, J=7.9 Hz, 2H, H-2' and H-6')[a], 7.96 (d, J=8.7 Hz, 1H, H-5), 7.90 (d, J=8.6 Hz, 2H, H-3' and H-5')[a], 6.96 (d, J=2.2 Hz, 1H, H-8), 6.94 (dd, J=8.8, 2.2 Hz, 1H, H-6). $\delta_C$ (151 MHz, DMSO-$d_6$): 102.4, 114.7, 115.6, 125.8, 127.1, 128.3, 129.3, 129.7, 135.9, 140.1, 142.7, 157.0, 163.3, 172.9. [a] Assignments may be interchangeable.

Example 30: 4'-Methylthio-3,7-dihydroxyflavone (3o)

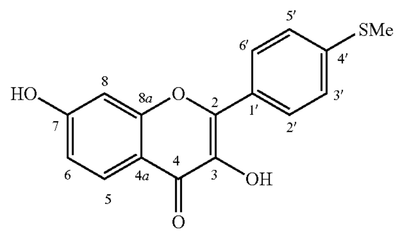

Starting from 0.093 g (0.285 mmol) was obtained as yellow crystals in a 42% yield (0.036 g) after crystallisation from methanol followed by hot filtration from toluene. HRMS (m/z): Calculated for [$M^+$] 300.0456; found 300.0420. $\delta_H$ (400 MHz, DMSO-$d_6$): 8.13 (d, J=8.8 Hz, 2H, H-5' and H-3'), 7.92 (d, J=8.7 Hz, 1H, H-5), 7.41 (d, J=8.8 Hz, 2H, H-2' and H-6'), 5.88-6.94 (m, 2H, H-6 and H-8), 2.54 (s, 3H, $SCH_3$). [a]Assignments may be interchangeable.

Example 3p: 4'-Methylsulfone-3,7-dihydroxyflavone (3p)

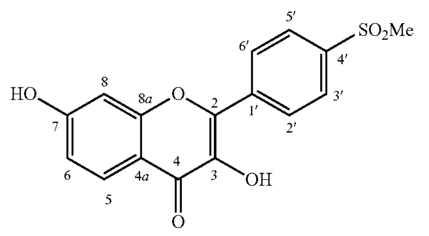 [SMILES: CS(=O)(=O)c1ccc(-c2oc3cc(O)ccc3c(=O)c2O)cc1]

Starting from 0.084 g (0.223 mmol) was obtained as yellow crystals in a 73% yield (0.054 g) after crystallisation from methanol. HRMS (m/z): Calculate for [$M^+$] 332.0355; found 332.0307. $\delta_H$ (400 MHz, DMSO-$d_6$): δ 10.87 (brs, 7-OH), 9.91 (brs, 3-OH), 8.40 (d, J=8.1 Hz, 2H, H-2' and H-6'), 8.07 (d, J=8.1 Hz, 2H, H-3' and H-5'), 7.95 (d, J=8.7 Hz, 1H, H-5), 7.13-6.82 (m, 2H, H-6 and H-8), 3.26 (s, 3H, $SO_2CH_3$). $\delta_C$ (101 MHz, DMSO-$d_6$): 172.9, 163.3, 157.1, 142.5, 141.2, 140.3, 136.7, 128.4, 127.6, 127.1, 115.6, 114.7, 102.5, 43.9. [a]Assignments may be interchangeable.

Figure 4:
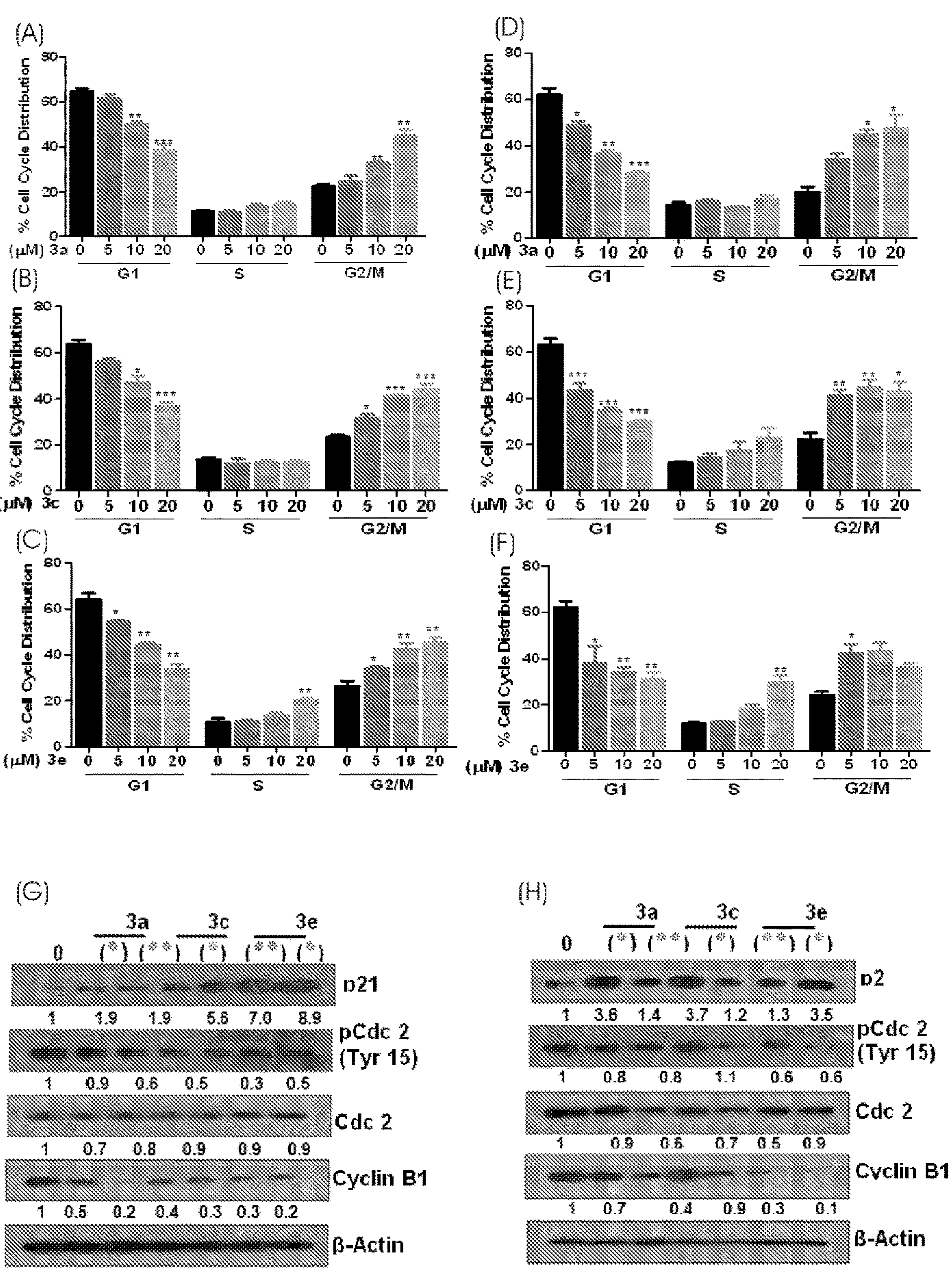
FIG. 4 shows the effect of Fisetin analogues on cell cycle distribution and molecular markers in A549 and H1299 cells.

Example 4: Inhibition of Cell Proliferation and Downregulation of the EGFR and Erk1/2 Pathway To evaluate the effect of Fisetin analogues 3a, 3c and 3e on cell proliferation and death of human lung cancer cells, trypan blue cell exclusion assays were performed. A549 and H1299 cancer cells were treated with different concentrations of three selected Fisetin analogues for 48 h. The Fisetin analogues decreased the viability of cells and caused cell death in both the cell lines in a concentration dependent fashion. A549 and H1299 cells were treated with 5, 10 and 20 μM of Fisetin analogues for 48 h. All three analogues decreased cell proliferation and induced cell death. The $IC_{50}$ concentrations for these analogues against A549 cells were calculated at 11.9 μM for analogue 3a (FIG. 4A left), 12.1 μM for analogue 3c (FIG. 4B left) and 12.3 μM for analogue 3e (FIG. 4C left) after 48 h. The effectiveness of the Fisetin analogues were even more pronounced against the more aggressive H1299 lung cancer cells, with $IC_{50}$ concentrations of 4.5 μM for analogue 3a (FIG. 4D left), 5.4 μM for analogue 3c (FIG. 4E left), and 3.1 μM for analogue 3e (FIG. 4F left).

Similarly, these analogues induced cell death in both A549 and H1299 cells. Analogue 3a caused a 4.8 to 12% cell death at 5-20 μM concentrations, compared to 2.4% in control cells (FIG. 4A right). Analogue 3c caused a 6.4 to 12.5% cell death (FIG. 4B right), and analogue 3e caused a 4.5 to 14.5% cell death (FIG. 4C right).

Similarly, in H1299 cells analogue 3a induced a 11.7 to 14.9% cell death (FIG. 4D right) compared to 3.8% in control cells. Analogue 3c (FIG. 4E right) and analogue 3e (FIG. 4F right) induced cell death of 8.2 to 15.1% and 8.8 to 16.6% respectively. For western blot experiments, two concentrations were used, i.e. the $IC_{50}$ concentration and the next higher concentration utilized for cell proliferation for each cell line. For instance, the higher concentration used for A549 was 20 μM ($IC_{50}$ 11.9 to 12.1 μM), and for H1299 it was 10 μM ($IC_{50}$ 3.1 to 5.4 μM).

The expression of pro-oncogenic signalling molecules, which are involved in proliferation and survival of cancer cells, were evaluated. In A549 cells (FIG. 4G), the expression of phospho-EGFR was analysed, and it was found that it was minimally affected except for higher concentration of analogue 3c, the total amount of EGFR was not affected by any of the treatments. The expression of pErk1/2 in A549 cells (FIG. 4G) was also evaluated and it was found that all three Fisetin analogues 3a, 3c and 3e decreased the expression of phospho-Erk1/2 significantly at both the concentrations; however, the total form of Erk1/2 was not affected except for 3c in the higher concentration.

The expression of phospho-EGFR in H1299 cells (FIG. 4H) was evaluated and it was found that a lower concentration of analogue 3a did not affect the expression of both phospho and total EGFR, however, higher concentration of analogue 3a significantly decreased the expression of both phospho and total EGFR. Also, analogue 3c decreased the expression of both phospho and total EGFR, analogue 3e did not affect the expression levels of total EGFR but significantly decreased the expression of phospho-EGFR. In H1299 cells (FIG. 4H), the higher concentrations of all three Fisetin analogues decreased the expression of pErk1/2. Analogues 3c and 3e also decreased the expression of total Erk1/2 significantly.

Figure 5:
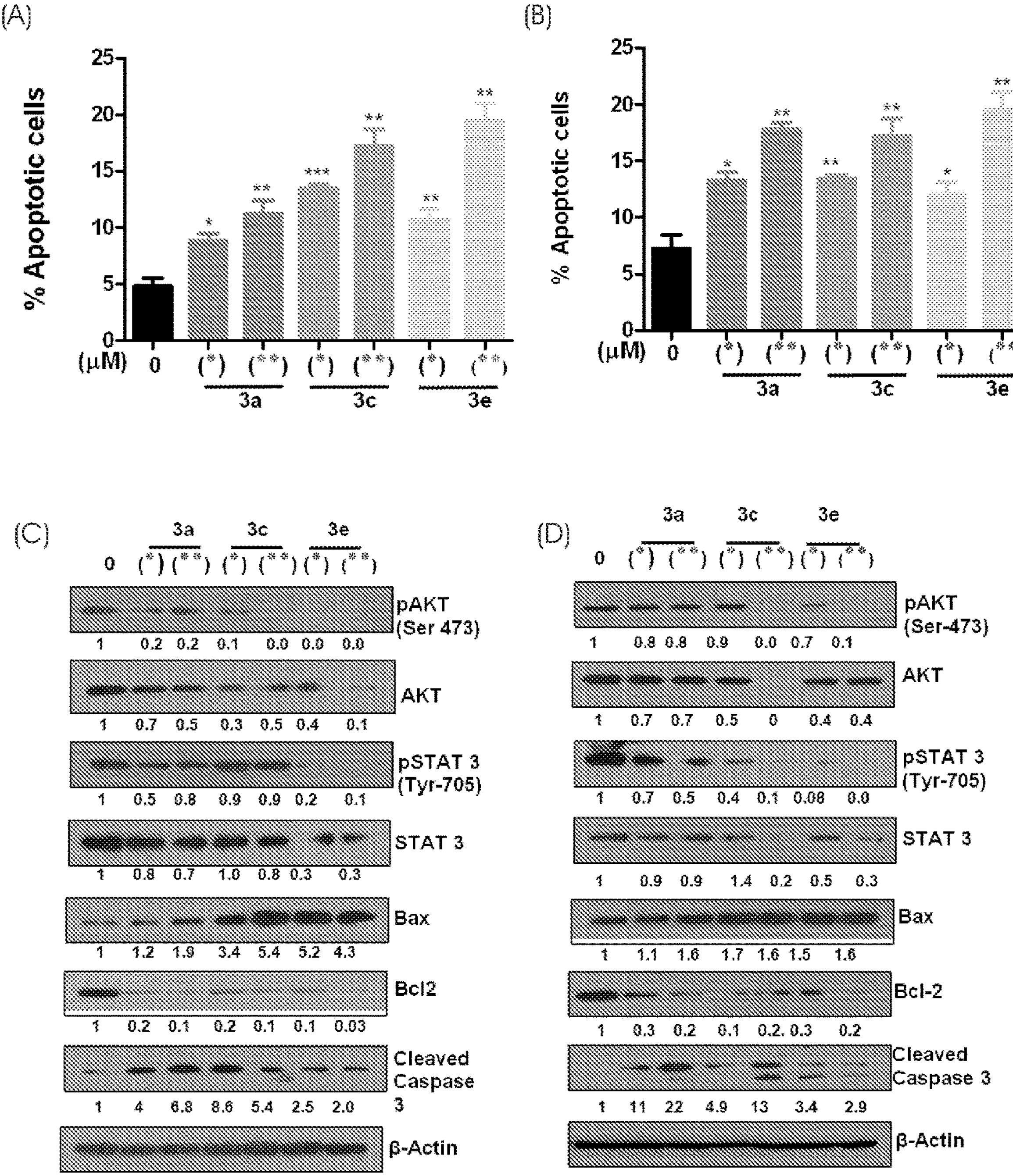
FIG. 5 shows the effect of Fisetin analogues on apoptotic death in human lung carcinoma cells.

Example 5: Induction of $G_2$/M Arrest and Modulation of the Expression of Cyclins/CDKS and CDKI To examine the effect of Fisetin analogues on cell cycle regulation, cells were treated with different concentrations of Fisetin analogues (5, 10 & 20 μM) for 48 h, then stained with propidium iodide and subjected to flow cytometry. All three of the tested Fisetin analogues induced $G_2$/M phase cell cycle arrest in A549 (FIGS. 5A-5C) and H1299 human lung cancer cells (FIGS. 5D-5F).

Higher concentrations (10 & 20 μM) of analogues 3a, 3c and 3e induced $G_2$/M phase arrest in both the cell lines significantly, however, analogue 3c at 5 μM also induced cell cycle arrest in A549 and H1299 cells. Also, analogue 3e at 5 μM induced $G_2$/M phase arrest in H1299 cells. In addition, analogue 3e also induced S-phase arrest at 20 μM concentration.

The effect of the Fisetin analogues on the expression levels of $G_2$/M phase specific cell cycle regulators were further investigated, by evaluating the effect of analogues 3a, 3c and 3e on the expression of p21, which are found to be downregulated in various cancers including lung cancers. In A549 cells, it was found that analogue 3a increased the expression of p21 marginally at both the concentrations, however, analogue 3c increased the p21 expression significantly at higher concentration, while analogue 3e increased the p21 expression to a much higher level at both the concentrations (FIG. 5G).

The expression of phospho Cdc-2 was investigated, as it is up-regulated in various cancers. In A549 cells (FIG. 5G) it was found that analogue 3a slightly decreased the phospho form of Cdc-2 at higher concentration, for analogues 3c and 3e, $IC_{50}$ concentration decreased the expression to some extent, however, the higher concentrations decreased the phospho-Cdc-2 expression significantly. The expression of total Cdc-2 was also evaluated, and it was found that the total Cdc-2 expression was not affected with these treatments. In addition, the $G_2$/M phase specific Cyclin B1 was evaluated, and a significant decrease in the expression of Cyclin B in A549 cells (FIG. 5G) was observed upon treatment with all three analogues. In the case of H1299 cells (FIG. 5H), p21 expression was significantly up regulated at higher concentrations of all three analogues, while at lower concentrations the expression was marginally higher compared to control. Phospho-Cdc-2 expression was marginally decreased in analogue 3a treatment; however, higher concentration of analogue 3c and both concentrations of analogue 3e decreased the expression of phospho-Cdc-2. Total Cdc-2 was marginally affected by higher concentration of analogues 3a and 3c, and no effect was seen for analogue 3e. The expression of Cyclin B1 was analysed, and it was found to be decreased in all treatments, except for the lower concentration of analogue 3c.

This modulation of Cyclin-CDKs and CDKIs explain the $G_2$/M phase arrest induced by the Fisetin analogues at molecular level.

Example 6: Induction of Apoptosis and Modulation of the Expression of Apoptosis Markers in A549 and H1299 Cells A549 and H1299 cells were treated with the $IC_{50}$ concentration and the corresponding higher concentrations (20 μM and 10 μM for A549 and H1299 respectively) of analogues 3a, 3c and 3e for 48 h and an apoptosis assay was performed. In A549, analogue 3a induced 8.2 and 11.2% apoptosis, analogue 3c induced 13.4 and 17.2% apoptosis, and analogue 3e induced 10.6 to 19.5% apoptosis compared to 4.7% in control cells (FIG. 6A).

In H1299 cancer cells, analogue 3a induced 13.2 and 17.8% apoptosis, analogue 3c induced 13.4 and 17.2% apoptosis, and analogue 3e induced 12.1 and 19.5% apoptosis.

The effect of the Fisetin analogues on molecular markers of apoptosis was assessed. In A549 cells (FIG. 6C), Phospho-Akt was found to be down-regulated upon Fisetin analogues treatment, the total form of Akt was slightly downregulated for analogues 3a and 3c, however, analogue 3e decreased the expression of total Akt at both the concentrations (FIG. 6C). The expression of phospho-Stat-3 in A549 cells (FIG. 6C) was evaluated, and it was found that analogue 3c decreased the expression of p-Stat-3 at both the concentrations; analogue 3c did not affect the levels of p-Stat-3, while analogue 3e completely abolished the expression of p-Stat-3. The total Stat-3 expression was not affected by treatment with analogues 3a and 3c, while treatment with analogue 3e significantly decreased the expression of total Stat-3 (FIG. 6C).

Figure 6:
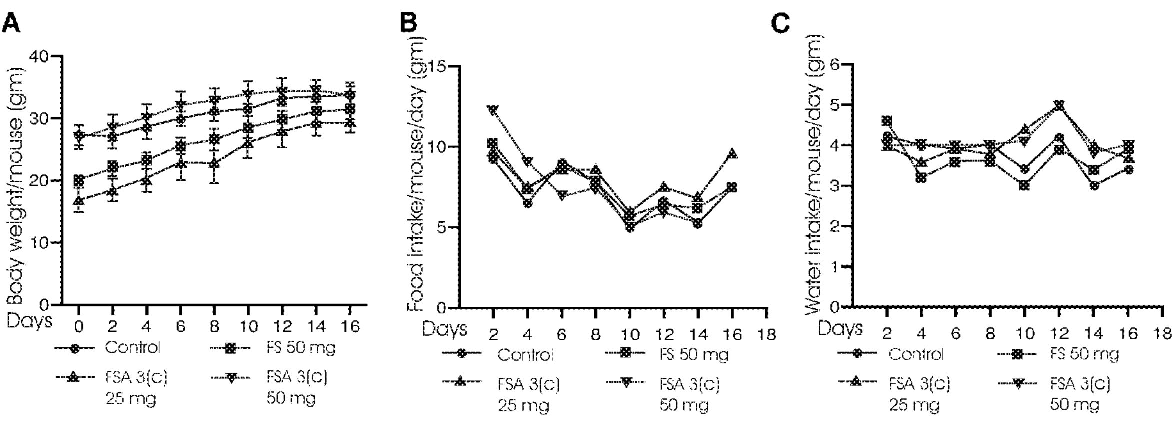
FIG. 6 shows that Fisetin and Fisetin analogue 3c did not cause toxicity in swiss albino mice.
Figure 6:
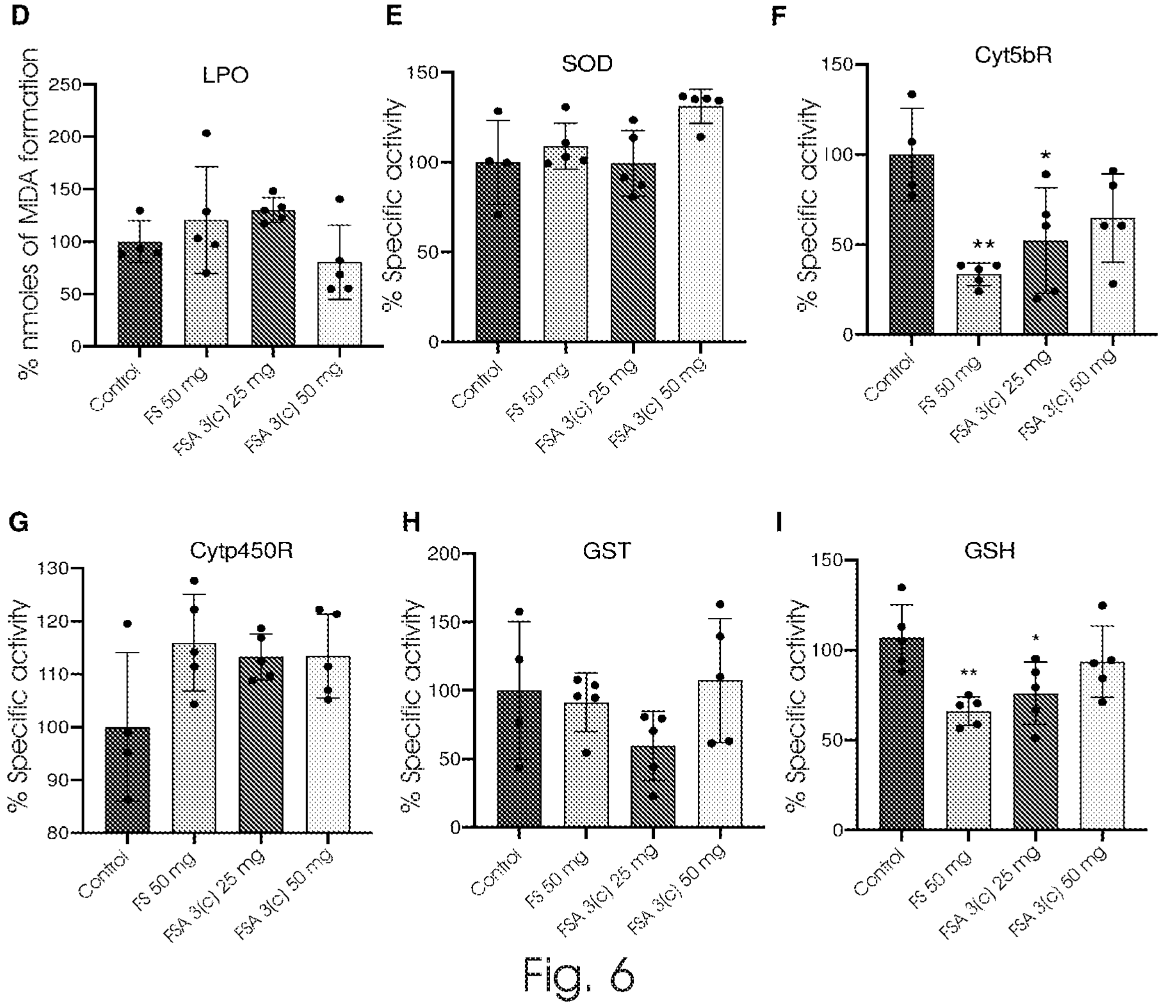

In H1299 cells (FIG. 6D), analogue 3a did not affect the expression of phospho and total Akt at both the concentrations, while with analogue 3c, both phospho and total Akt were completely undetected, analogue 3e significantly decrease the phospho Akt, but did not affect the total Akt (FIG. 6D). All three the Fisetin analogues decreased the expression of phospho-Stat-3 significantly; analogues 3c and 3e also decreased the expression of total Stat-3 at higher concentrations (FIG. 6D). The decreased expression of these proteins explains the decreased cell proliferation in both A549 and H1299 cells. Furthermore, in A549 cells (FIG. 6C), analogue 3a slightly increased the expression of pro-apoptotic protein Bax, however, analogues 3c and 3e increased the expression of Bax with much higher potential. Inversely, the expression level of anti-apoptotic protein Bcl-2 was found to be significantly lower when treated with all three the Fisetin analogues. Further, it was found that analogue 3a increased the cleavage of caspase-3 significantly, while the $IC_{50}$ concentration of analogue 3c also increased cleaved caspase-3 to a significant amount, however, higher concentration of analogue 3c and both the concentrations of analogue 3e increased the cleaved caspase-3 marginally compared to control cells. In H1299 cells (FIG. 6D), the expression of Bax was slightly higher after analogue 3a treatment; however, both analogues 3c and 3e increased the expression of pro-apoptotic protein Bax. Consistent with A549 data, all three the Fisetin analogues decreased the expression of anti-apoptotic protein Bcl-2 at both the concentrations. In H1299 cells, all the analogues increased cleaved Caspase-3 compared to control untreated cells. Thus, modulation of apoptosis regulatory proteins has caused apoptosis in both A549 and H1299 cells by the tested Fisetin analogues.

Example 7: Toxicity of Fisetin Analogue 3c

Fisetin analogue 3c was used to assess the potential toxicity of these analogues in a pre-clinical model. To test the acute toxicity, Fisetin (50 mg/kg body weight), analogue 3c (25 mg/kg and 50 mg/kg body weight), and vehicle control (5% DMSO, 45% PEG-300 and 50% saline) was fed orally for two weeks. Abnormal clinical signs such as decreased motor activity, sensory reflection, body weight, food intake, and water intake were monitored during the treatment period. An increase in body weight was observed among all groups throughout the treatment period (FIG. 7A). In respect of food and water consumption, all groups showed variation in their eating and drinking behaviour during the treatment duration (FIGS. 7B and 7C). This variation could be due to consistent frequency of dosage. Overall, these observations suggest that the Fisetin analogues, in particular analogue 3c, should be well tolerated in animal models.

Example 8: Hepatotoxicity of Fisetin Analogue 3c

Hepatotoxicity is considered to be one of the major challenges for drug development schemes. The liver is the primary organ for the metabolism or biotransformation of a given drug. To assess the hepatotoxicity of these compounds, the effects of Fisetin and analogue 3c on various hepatic enzymes was assessed.

A lipid peroxidation assay was performed on microsomal liver fraction and determined in terms of TBARS formation.

No significant change in the MDA formation (FIG. 70) was observed. Next, specific activity of SOD was measured and it found to moderately induced with Fisetin and its analogue 3c which suggest the antioxidant status in in vivo model (FIG. 7E). The modulatory effects of Fisetin and analogue 3c were determined on the specific activities of cytochrome b5 reductase (Cytb5R) and cytochrome P450 reductase (CytP450R), phase I enzyme of xenobiotic metabolism. Fisetin and analogue 3c caused reduction in the specific activity of cytochrome b5 reductase. Fisetin decreased Cytb5R specific activity by 66% whereas analogue 3c (50 mg/kg) caused a 36% reduction in specific activity (FIG. 7F). An increase in specific activity of CytP450R by Fisetin and analogue 3c was observed. Fisetin and analogue 3c (50 mg/kg) increased the specific activity by 15% and 13%, respectively (FIG. 7G). Next, the specific activities of phase II enzymes, glutathione S-transferase (GST) and reduced glutathione (GSH) were measured. Fisetin and analogue 3c did not cause significant change in the specific activities of GST as compared to the control group (FIG. 7H). Fisetin and analogue 3c (50 mg/kg) caused a decrease in specific activity of GSH by 34% and 7%, respectively (FIG. 7I). Overall, these different parameters with respect of hepatotoxicity, suggest that Fisetin analogue 3c (CK08) does not show toxicity in in vivo models. These analogues are therefore likely to be effective and safe phytochemicals.

Example 9: Fisetin Analogue 3c Inhibits B(a)P-induced Lung Carcinogenesis in Swiss Albino Mice To assess whether Fisetin and its 4-bromo-Fisetin analogue (Fisetin analogue 3c) have anticarcinogenesis activity and if any toxicity in terms of water and food consumption, and body weight, Benzo[a]pyrene [B(a)P] induced lung carcinogenesis in Swiss albino mice were employed in the study. Along with the antitumor activity of the agents, the body weight, food and water intake in different treatment groups were monitored on regular intervals and analysed.

There were six different treatment groups in the study including, (1) control, (2) B(a)P, (3) Fisetin+B(a)P, (4) Fisetin analogue 3c+B(a)P, (5) B(a)P+Fisetin and (6) B(a)P+Fisetin analogue 3c.

Figure 9:
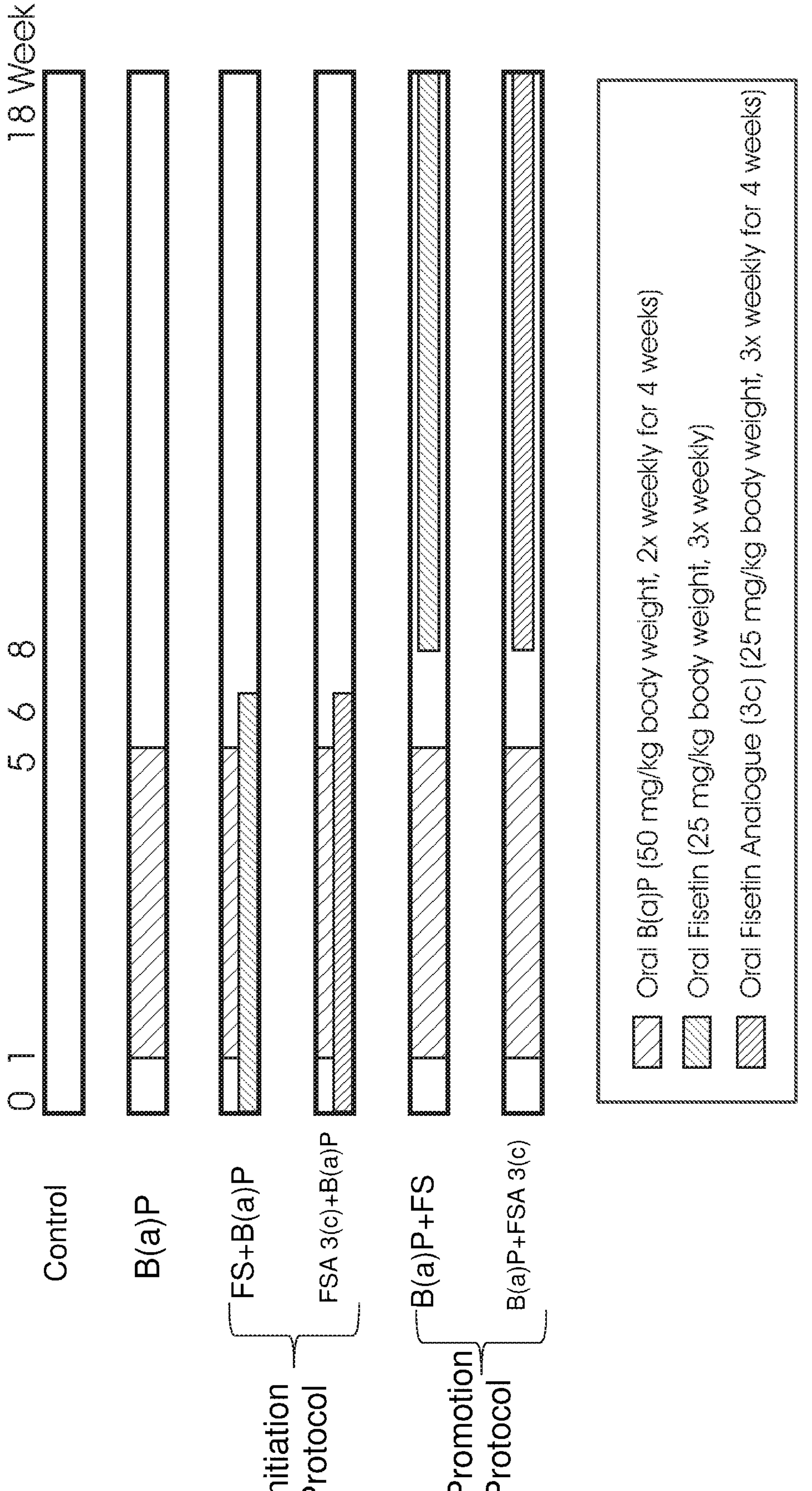
FIG. 9 shows the experimental design to study the effects of Fisetin and 4'-bromo Fisetin analogue (3c) on B(a)P-induced lung carcinogenesis in Swiss albino mice.

Groups 3 and 4 represent the Initiation Protocol (agents treatment started 1 week before carcinogen treatment and continued 1 week after the last dose of the carcinogen). Groups 5 and 6 represent the Promotion Protocol (agents treatment started after 3 weeks of the carcinogen treatment). The B(a)P was given orally twice a week for 4 weeks at 50 mg/kg body weight dose, whereas Fisetin and Fisetin analogue (3c) were administered orally at 25 mg/kg body weight thrice weekly (see FIG. 9).

Figure 10:
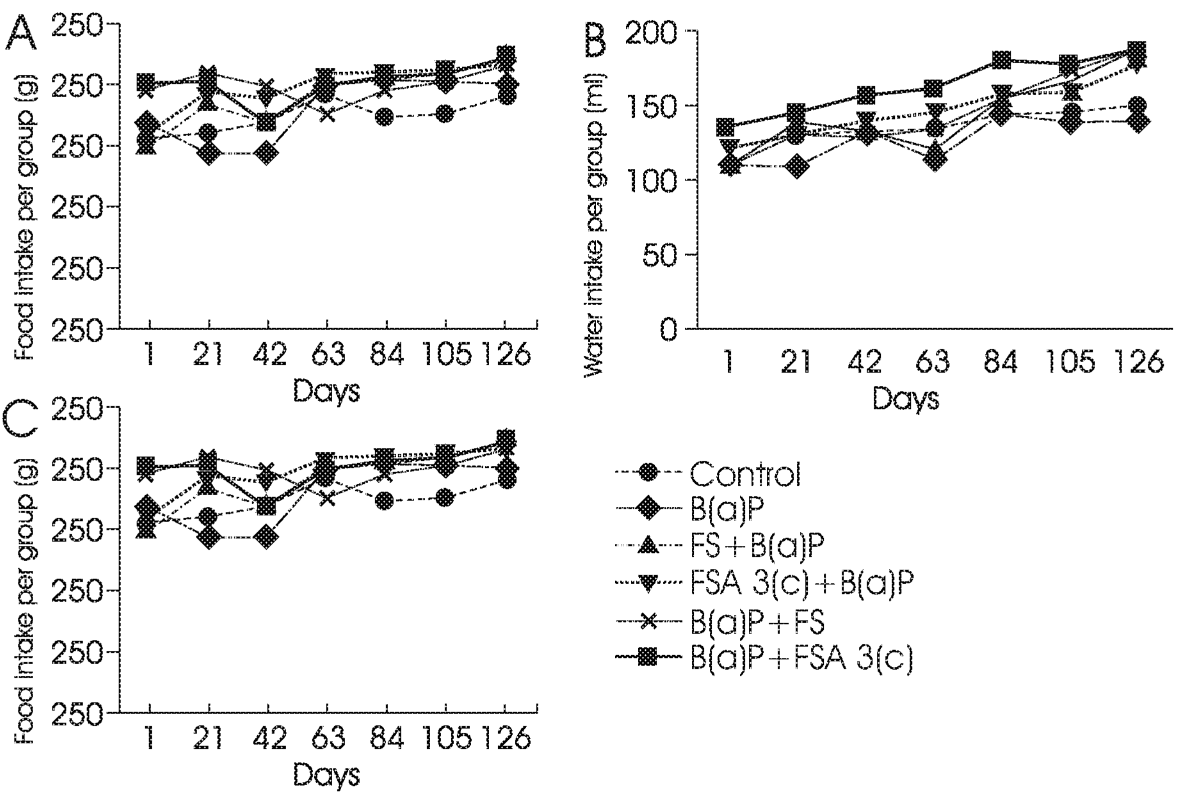
FIG. 10 shows the effects of Fisetin (FS) and 4'-bromo Fisetin analogue (3c) on B(a)P-induced lung carcinogenesis in Swiss albino mice. (A) Food consumption in each group, (B) Water intake in each group, (C) Body weight of mouse in each group, and (D) Tumor lesion incidence in lung through gross observation and histopathology.

There was a steady increment observed for the food consumption by the mice in all the groups except in the case of the carcinogen B(a)P only group, where during day 1 to day 42 the food consumption rate was lower as compared to all other groups (FIG. 10A).

A similar trend was observed in water intake in all groups beginning from day 1 to day 126 of the experiment, but in case of only carcinogen [B(a)P] treated group, the level of water intake was lesser as compared to other treatment groups. Water intake level were normal in all groups treated with Fisetin analogue 3c or Fisetin (FIG. 10B).

Further, weight gain in groups treated with Fisetin analogue 3c and Fisetin in both Initiation and Promotion Protocol groups were higher as compared to the other groups, specifically, the weight gain profile in only B(a)P induced lung carcinogenesis group was found to be lower throughout the experiment (FIG. 10C). These findings suggest that consumption of both 4'-bromo-Fisetin analogue 3c and Fisetin did not show any systemic toxicity during the long-term of its application and are safe for consumption.

Figure 11:
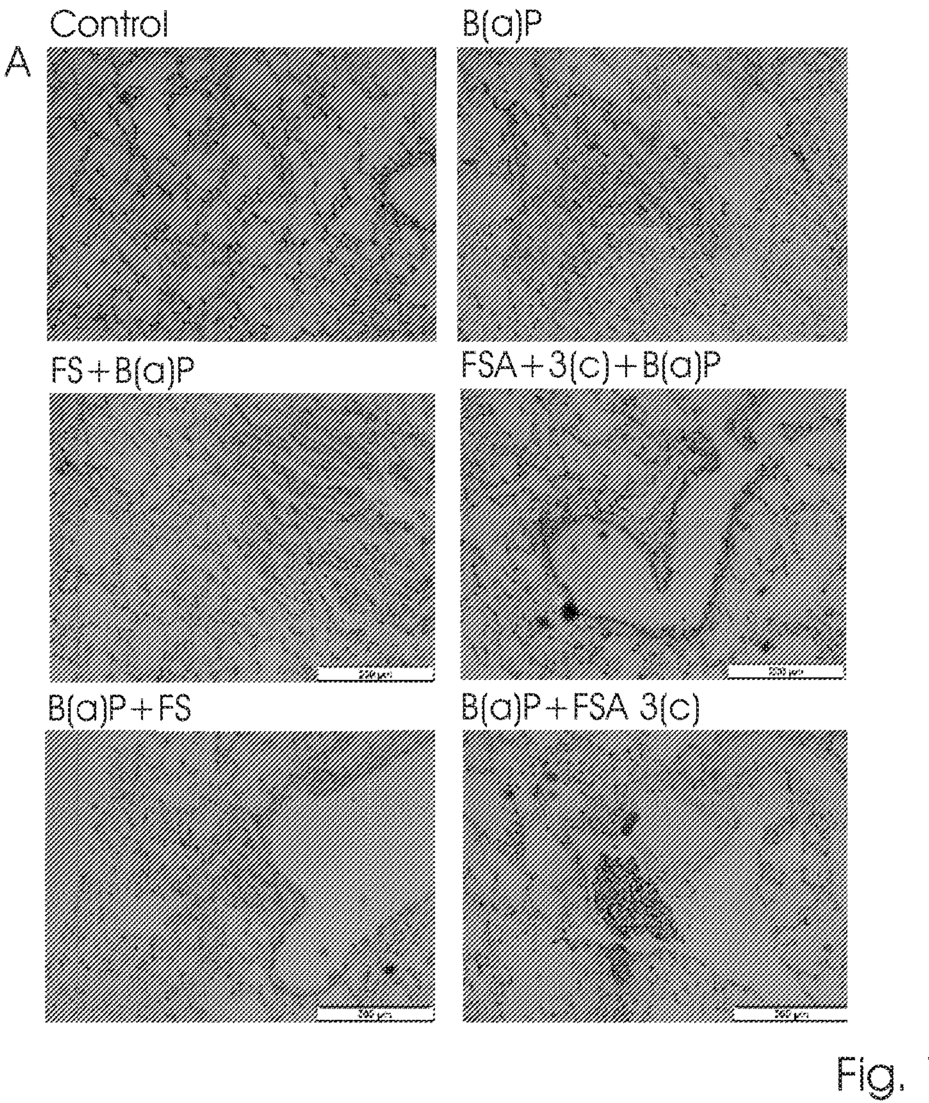
FIG. 11 shows the efficacy of Fisetin and 4'-bromo Fisetin analogue (3c) in B(a)P-induced lung carcinogenesis in Swiss albino mice. Tumor lesion burden in each group was analysed: (A) Hematoxylin and Eosin stain of mice lungs at 200× magnification, showing tumor lesion, (B) Number of lesions per group and per mouse in each group, and (C) Total area of lesions were measured and presented in micrometer square for each group.
Figure 11:
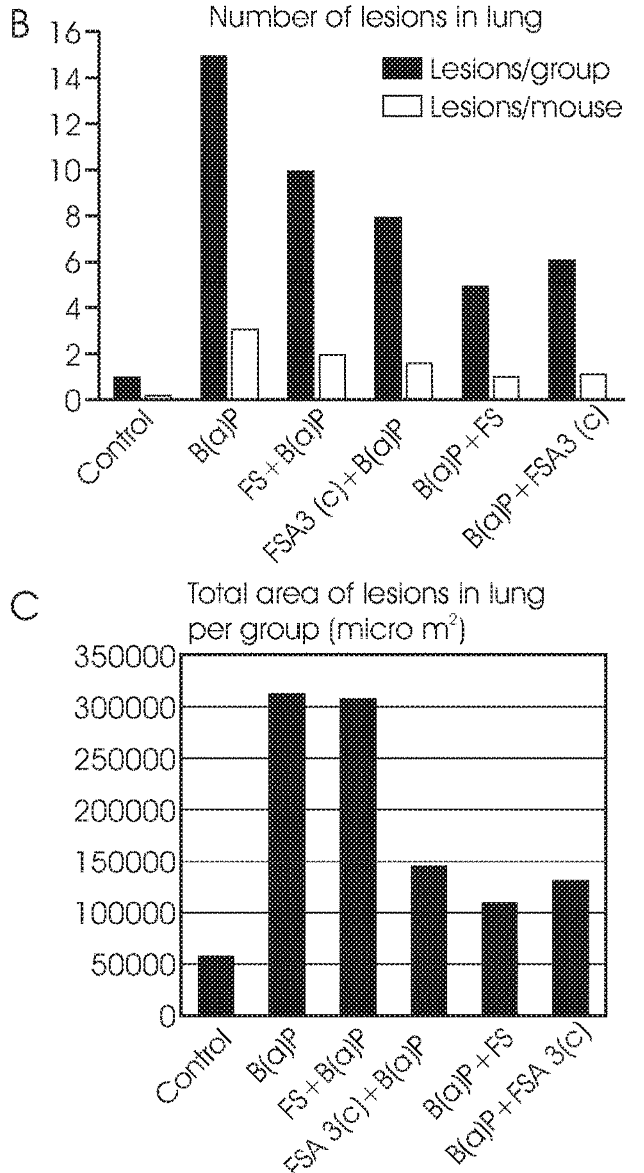

Tumor incidence was evaluated in each test group, with the results represented in FIG. 10D. External surface and gross observation of lung showed 100% tumor incidence in the carcinogen B(a)P-treated group and reduction of tumor incidence was noticed in all other treatment groups. The 4'-bromo-Fisetin analogue 3c was effective when applied during the tumor initiation phase, and only one mouse showed surface tumor lesion out of five. For an overall assessment of tumor lesions in different groups, serial sectioning of lung was done and histopathological observation of hematoxylin and eosin (H&E) stained serial sections showed that tumor incidence is less in 4'-bromo-Fisetin analogue 3c and Fisetin treated groups as compared to the carcinogen treated group (FIG. 11A).

The variation in microscopic images captured for each group suggested that in B(a)P-induced carcinogenesis group there are larger-sized deep stained nuclei and loss, or shrinkage, of alveoli as compared to the control and 4'-bromo-Fisetin analogue 3c and Fisetin treated groups. 4-bromo-Fisetin analogue 3c and Fisetin treatments showed reversal of the tumorigenic features including the size of nucleus, cytoplasmic content and alveoli. As can be seen from FIG. 11A, among the treatment groups, during the initiation phase of mice treated with 4'-bromo-Fisetin analogue 3c and Fisetin, the analogue showed very efficient recovery of nuclei and alveoli structure similar to the control group.

The tumor lesions per mouse and total number of lesions per group also showed similar results wherein B(a)P-induced tumor lesions were strongly reduced in 4'-bromo-Fisetin analogue 3c and Fisetin treated groups. In case of tumor initiation group treated with 4'-bromo-Fisetin analogue 3c, the total number of lesions were reduced by approximately 50%, and in tumor promotion group, 4'-bromo-Fisetin analogue 3c as well as Fisetin showed more than 50% reduction in the total number of lesions observed. Also, the lesions per mouse in the 4'-bromo-Fisetin analogue 3c and Fisetin treated group were reduced and the highest reduction was found in the promotion group with Fisetin and 4'-bromo-Fisetin analogue 3c (FIG. 11B).

The area or size of tumor lesions were also measured in each group. The assessment of tumor lesion area indicated that the carcinogen B(a)P-treated and Fisetin-treated groups during tumor initiation phase were having similar larger sized lesions. More importantly, the area or size of lesions were decreased by approximately 50% in the initiation group and more than 50% in the promotion group treated with 4'-bromo-Fisetin analogue (3c). The parent compound Fisetin was not effective as compared to the analogue in the initiation protocol (FIG. 11C).

In summary, 4-bromo Fisetin analogue 3c has been shown to be efficacious in inhibiting B(a)P induced lung carcinogenesis in a mouse model. In the Initiation Protocol, the 4'-bromo Fisetin analogue 3c was more effective in reducing the number as well as the size of the lung tumor lesions as compared to the parent compound Fisetin. The long-term administration of both the agents were non-toxic to the animals.

The invention claimed is:

1. A method of treating cancer in a subject in need thereof, the method comprising administering a therapeutically effective amount of the compound of Formula I:

I

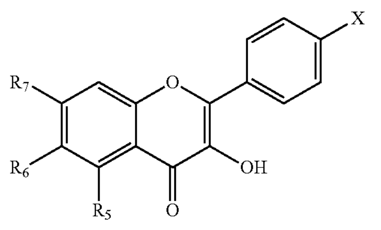

or a pharmaceutically acceptable salt or solvate thereof, wherein:

X is a ring deactivating group selected from $-SO_2F$, $-SF_5$, $-NO$, $-SO_2NH_2$, $-CF_3$, $-OCF_3$, $-SCF_3$, $-NCS$, $-SCN$, $-SO_2CF_3$, $-CHO$, $-CONH_2$, $-SOCH_3$, $-OSO_2CH_3$, $-SO_2CH_3$, $-CF_2CF_3$, $-CH{=}CHNO_2$, $-COCH_3$, $-SCOCH_3$, $-CO_2C_2H_5$, $-CO_2CH_3$, $-CONHCH_3$, $-SO_2C_2H_5$, $-COC_3H_7$, $-N{=}NC_6H_5$, $-SO_2C_6H_5$, and $-OSO_2C_6H_5$; and $R_7$, $R_6$, and $R_5$ are independently selected from H, OH, $-O(CH_2)OR_4$, and $-OR_4$, provided that at least one of $R_7$, $R_6$, and $R_5$ is OH, $-O(CH_2)OR_4$, or $-OR_4$; and $R_4$ is selected from the group consisting of $C_1$-$C_6$ alkyl, $C_1$-$C_6$ heteroalkyl, $C_1$-$C_6$ aryl, and $C_1$-$C_6$ heteroaryl.

2. The method of claim 1, wherein X is selected from $CF_3$ and $SO_2CH_3$.

3. The method of claim 1, wherein $R_6$, and $R_5$ are H and $R_7$ is OH.

4. The method of claim 1, wherein $R_7$, and $R_5$ are H and $R_6$ is OH.

5. The method of claim 1, wherein $R_7$, and $R_6$ are H and $R_5$ is OH.

6. The method of claim 1, wherein $R_6$, and $R_5$ are H and $R_7$ is $-O(CH_2)OCH_3$.

7. The method of claim 1, wherein $R_7$, and $R_5$ are H and $R_6$ is $-O(CH_2)OCH_3$.

8. A pharmaceutical composition comprising a compound of Formula I:

I

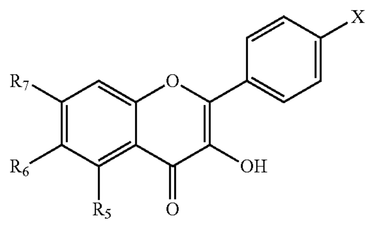

or a pharmaceutically acceptable salt or solvate thereof, and one or more pharmaceutically acceptable vehicles wherein:

X is a ring deactivating group selected from $-SO_2F$, $-SF_5$, $-NO$, $-SO_2NH_2$, $-CF_3$, $-OCF_3$, $-SCF_3$, $-NCS$, $-SCN$, $-SO_2CF_3$, $-CHO$, $-CONH_2$, $-SOCH_3$, $-OSO_2CH_3$, $-SO_2CH_3$, $-CF_2CF_3$, $-CH{=}CHNO_2$, $-COCH_3$, $-SCOCH_3$, $-CO_2C_2H_5$, $-CO_2CH_3$, $-CONHCH_3$, $-SO_2C_2H_5$, $-COC_3H_7$, $-N{=}NC_6H_5$, $-SO_2C_6H_5$, and $-OSO_2C_6H_5$; and $R_7$, $R_6$, and $R_5$ are independently selected from H, OH, $-O(CH_2)OR_4$, and $-OR_4$, provided that at least one of $R_7$, $R_6$, and $R_5$ is OH, $-O(CH_2)OR_4$, or $-OR_4$; and $R_4$ is selected from the group consisting of $C_1$-$C_6$ alkyl, $C_1$-$C_6$ heteroalkyl, $C_1$-$C_6$ aryl, and $C_1$-$C_6$ heteroaryl.

9. The method according to claim 1, wherein the cancer is selected from the group consisting of lung cancer, breast cancer, prostate cancer, cancer of the pancreas, and colon cancer.

10. The method according to claim 9, wherein the cancer is lung cancer.

11. The pharmaceutical composition according to claim 8, for use in a method of treating cancer in a subject, the method comprising administering a therapeutically effective amount of the pharmaceutical composition to the subject.

12. The pharmaceutical composition for use according to claim 11, wherein the cancer is selected from the group consisting of lung cancer, breast cancer, prostate cancer, cancer of the pancreas, and colon cancer.

13. The pharmaceutical composition for use according to claim 12, wherein the cancer is lung cancer.

14. A method of treating cancer in a subject, the method comprising administering a therapeutically effective amount of the pharmaceutical composition according to claim 8 to the subject.

15. The method according to claim 14, wherein the cancer is selected from the group consisting of lung cancer, breast cancer, prostate cancer, cancer of the pancreas, and colon cancer.

* * * * *